United States Patent
Chen et al.

(10) Patent No.: US 11,664,110 B2
(45) Date of Patent: May 30, 2023

(54) SYSTEM, METHOD AND PORTABLE DEVICES FOR DETECTION AND ENHANCEMENT OF SLEEP SPINDLES

(71) Applicant: New York University, New York, NY (US)

(72) Inventors: Zhe S. Chen, New York, NY (US); Prathamesh M. Kulkarni, New York, NY (US); Zhengdong Xiao, Woodside, NY (US); Jing Wang, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 44 days.

(21) Appl. No.: 16/591,150

(22) Filed: Oct. 2, 2019

(65) Prior Publication Data

US 2020/0105398 A1  Apr. 2, 2020

Related U.S. Application Data

(60) Provisional application No. 62/740,270, filed on Oct. 2, 2018.

(51) Int. Cl.
*G16H 20/70* (2018.01)
*G16H 40/63* (2018.01)
*G06N 3/08* (2023.01)

(52) U.S. Cl.
CPC ............... *G16H 20/70* (2018.01); *G06N 3/08* (2013.01); *G16H 40/63* (2018.01)

(58) Field of Classification Search
None
See application file for complete search history.

(56) References Cited

U.S. PATENT DOCUMENTS 5,732,696 A * 3/1998 Rapoport ............. A61B 5/4812
600/509
2013/0072775 A1 * 3/2013 Rogers ................... A61M 5/31
600/378

(Continued)

FOREIGN PATENT DOCUMENTS

WO  WO-2010107928 A2 *  9/2010  ........... A61B 5/0205

OTHER PUBLICATIONS

Coppieters't Wallant, Dorothée, Pierre Maquet, and Christophe Phillips. "Sleep spindles as an electrographic element: description and automatic detection methods." Neural Plasticity 2016 (2016). (Year: 2016).*

*Primary Examiner* — Lena Najarian
(74) *Attorney, Agent, or Firm* — Fay Kaplun & Marcin, LLP

(57) ABSTRACT

A method for administering stimulations to a sleeping subject is provided. The method includes obtaining brain wave data generated based on brain wave activity of the subject over a predetermined time frame and determining a spectral power ratio of a spindle band to delta and theta bands of the brain wave data at a time within the predetermined time frame. The spectral power ratio and brain wave data are sent to the input of a pretrained deep neural network to generate a probability score that sleep spindles are being detected in the brain wave activity. The method may continue to obtain brain wave data and analyze the data using the pretrained deep neural network. A determination that sleep spindles are detected may be made when the probability score is above a predetermined threshold score for a predetermined threshold period of time.

19 Claims, 28 Drawing Sheets

(56) References Cited

U.S. PATENT DOCUMENTS

| | | | |
|---|---|---|---|
| 2016/0038712 A1* | 2/2016 | Finsterle | H04S 1/00 |
| | | | 600/28 |
| 2018/0092600 A1* | 4/2018 | Simons | A61B 5/6803 |
| 2018/0140249 A1* | 5/2018 | Frohlich | A61B 5/7282 |
| 2018/0333558 A1* | 11/2018 | Levendowski | A61B 5/11 |
| 2018/0368717 A1* | 12/2018 | Soulet De Brugiere | |
| | | | H04B 11/00 |
| 2019/0294243 A1* | 9/2019 | Laszlo | G06N 20/00 |

\* cited by examiner

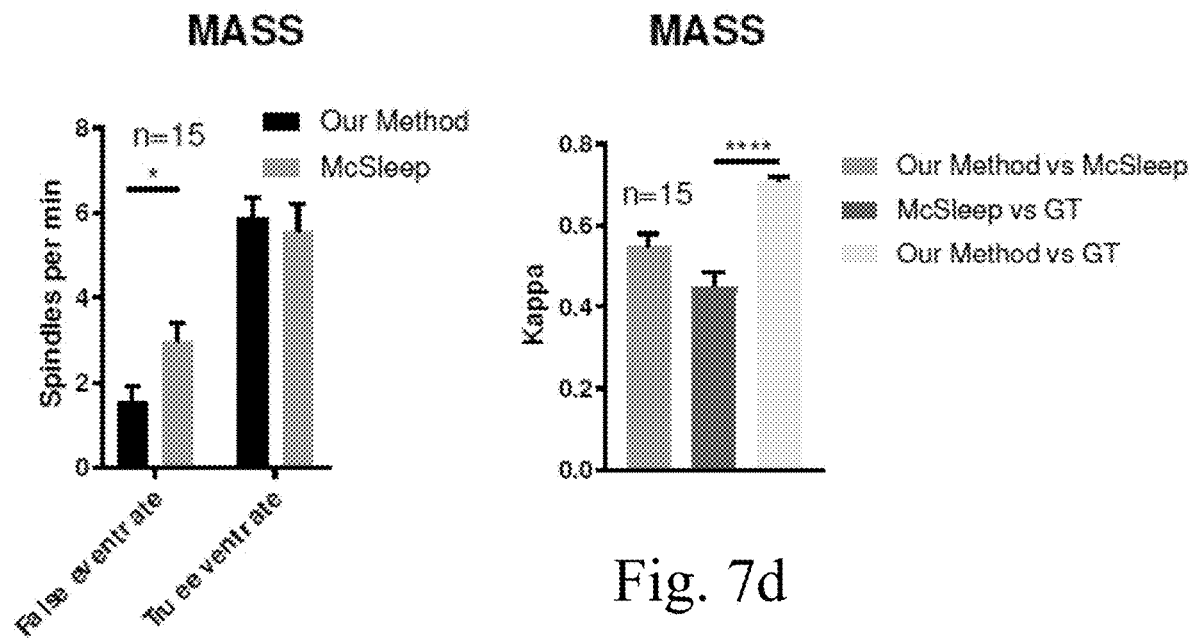
Fig. 7c
Fig. 7d
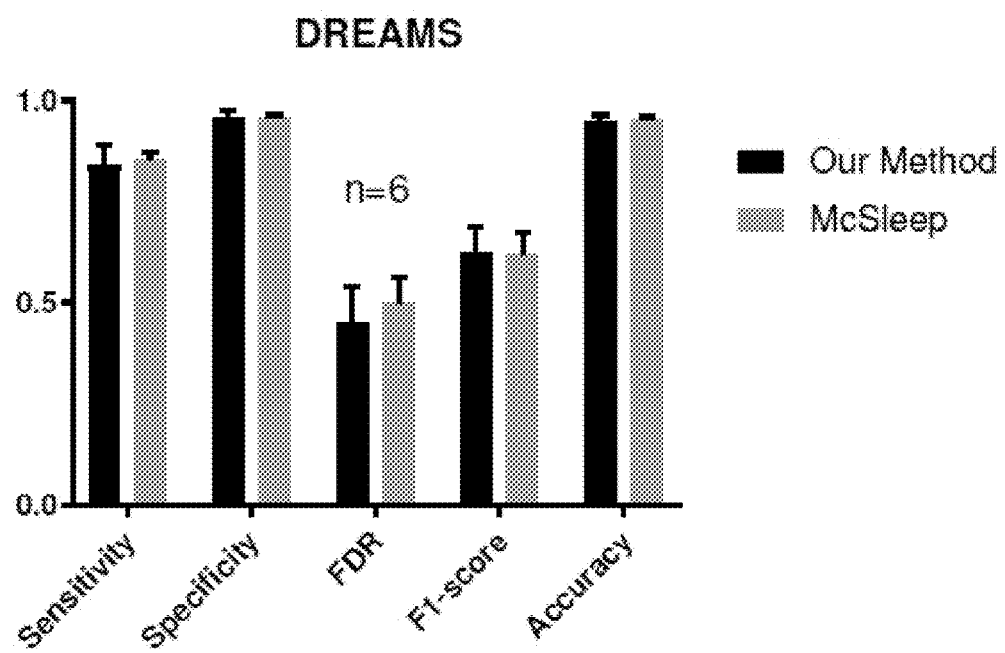
Fig. 7e

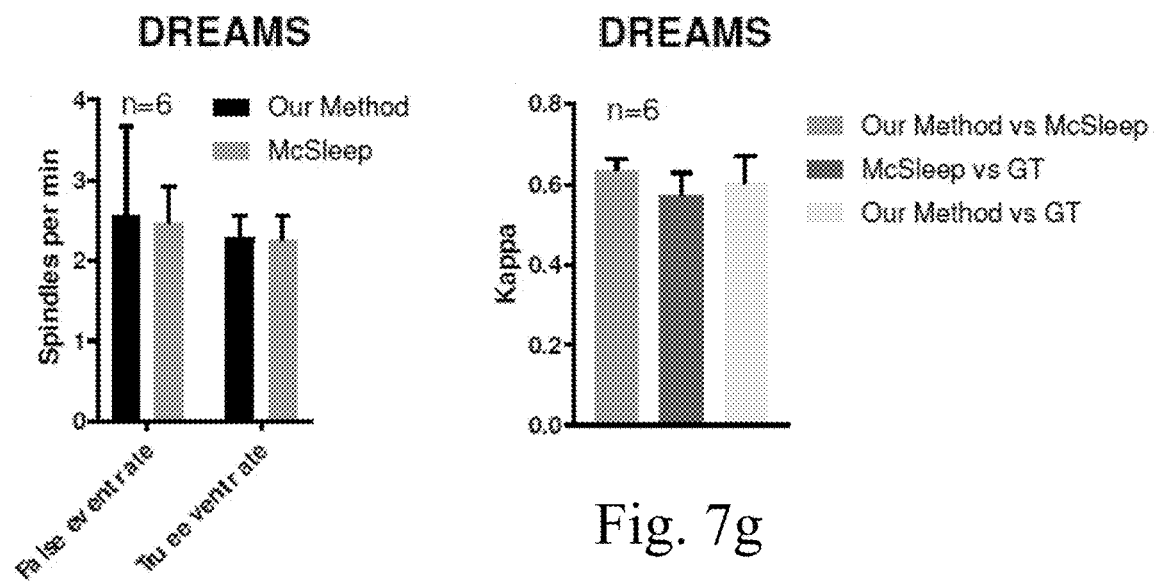
Fig. 7f
Fig. 7g
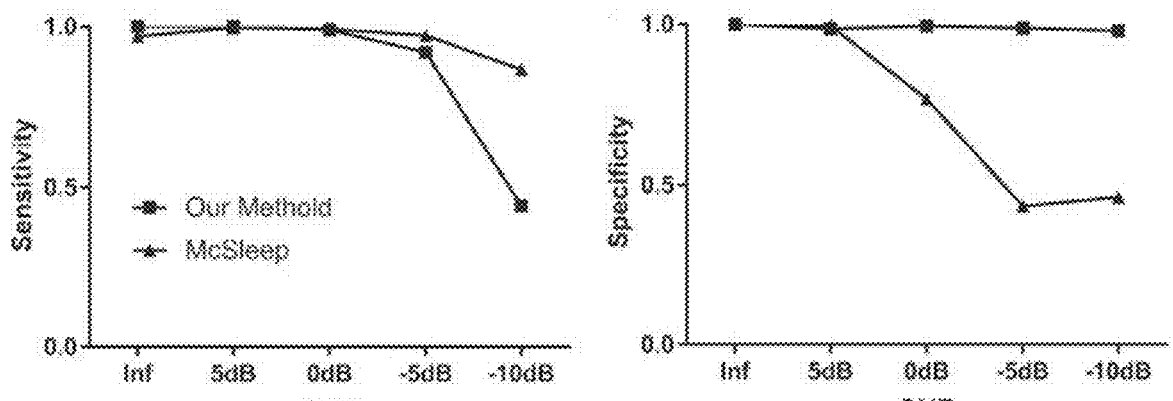
Fig. 8a
Fig. 8b

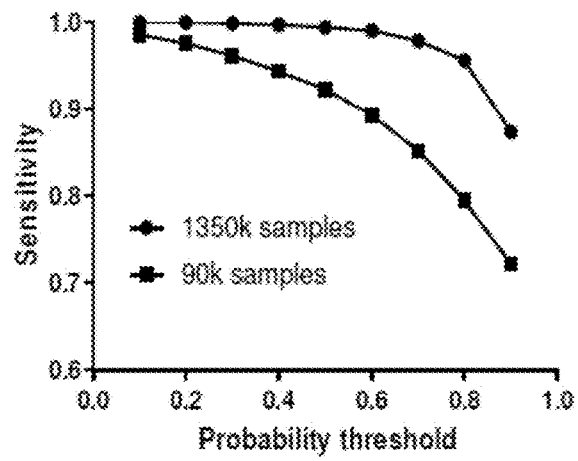
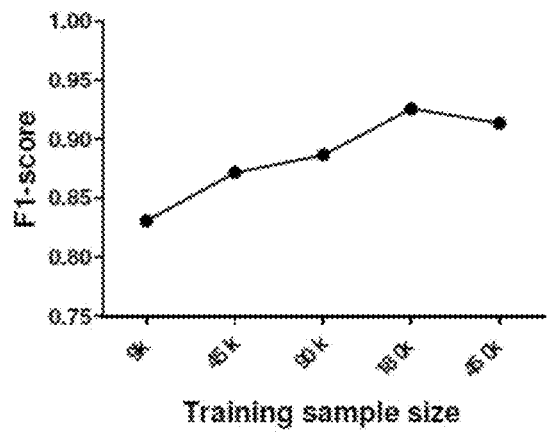
Fig. 9a　　　　Fig. 9b
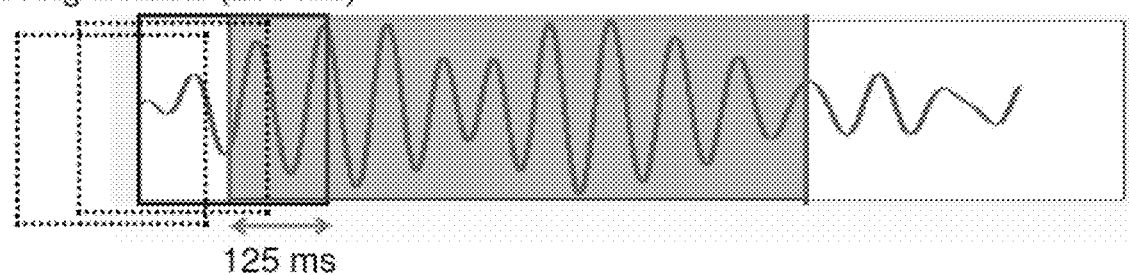
Fig. 10

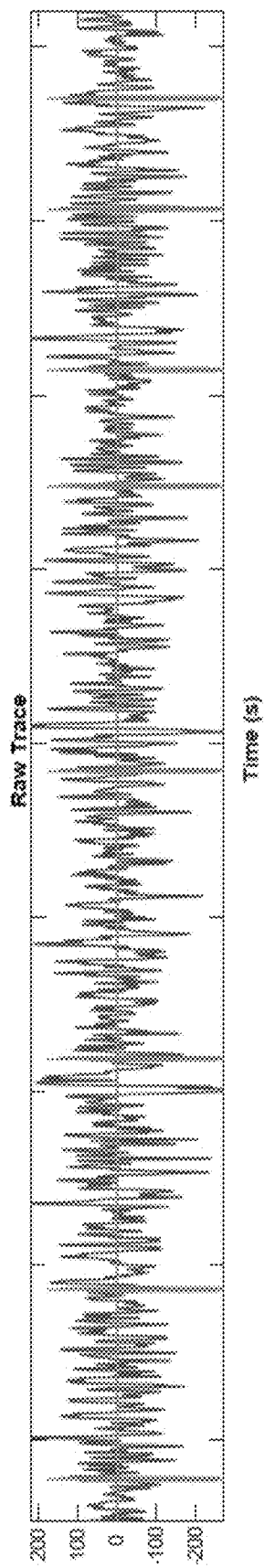
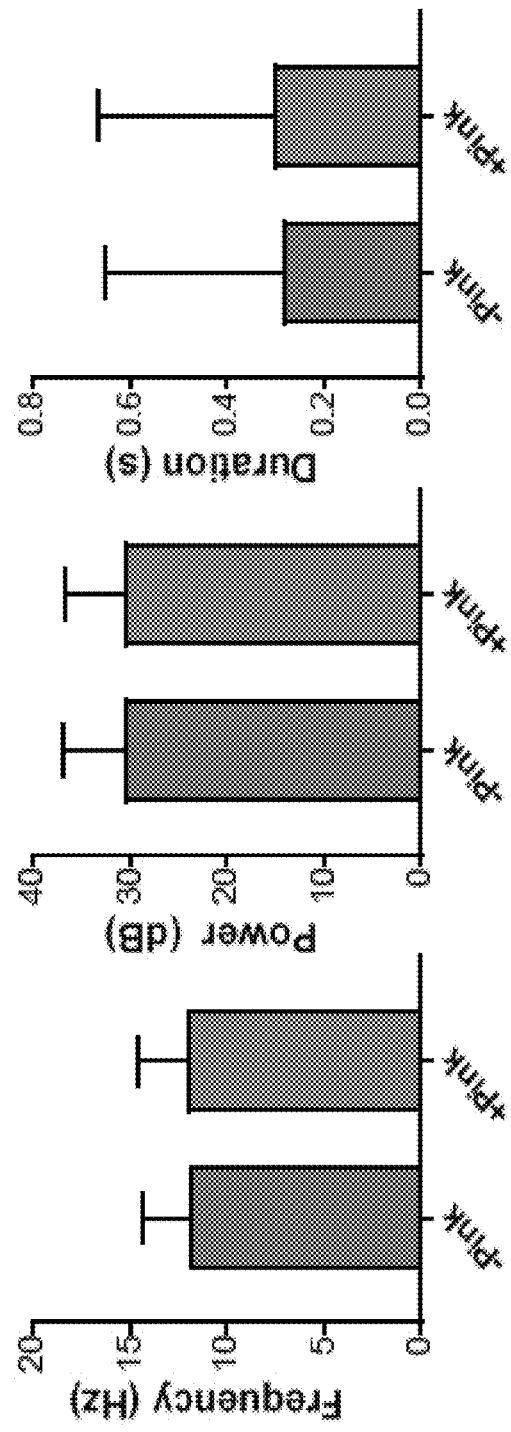
Fig. 22c
Fig. 22d

SYSTEM, METHOD AND PORTABLE DEVICES FOR DETECTION AND ENHANCEMENT OF SLEEP SPINDLES

PRIORITY CLAIM

The present application claims priority to U.S. Provisional Application Ser. No. 62/740,270 entitled "System, Method and Portable Devices for Real-Time Detection and Closed Loop Enhancement of Sleep Spindles" filed on Oct. 2, 2018, the entire contents of which is hereby incorporated by reference herein.

GOVERNMENT SUPPORT

This invention was made with government support under NSF Grant No. CBET-1835000 awarded by the National Science Foundation, and NIH Grant Nos. R01-MH118928 and R01-NS100065 awarded by the National Institute of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Sleep spindles are brief bursts of neural oscillations (9-16 or 11-16 Hz, 0.5-3 sec) generated by the interplay of the thalamic reticular nucleus and other thalamic nuclei during NREM sleep (N2 and N3 stages). While spindle waves are generated by the thalamus, they are relayed through thalamocortical oscillations to the cortex. Spindles can be observed in a wide range of thalamic and neocortical structures, and are temporally coupled with neocortical slow oscillations (SOs, 0.5-1 Hz) and hippocampal sharp-wave ripples (SWRs, 150-250 Hz) during NREM sleep. It is believed that spindles have functions in both memory consolidation and sensory processing. Spindles and SOs might have differential roles in memory consolidation at different sleep stages, or for consolidation of different types of memory traces. In addition, spindles are thought to contribute to a number of neural processes, such as somatosensory development, thalamocortical sensory gating, and synaptic plasticity. Spindles have also been implicated in integrating new memories with existing knowledge. Deficits in spindle activity during sleep are believed to be linked to numerous pathologies including epilepsy and other neuropsychiatric illness. It is believed that spindles are involved in the attenuation of signals from the external environment, suggesting a role for spindle waves in processing nociceptive inputs.

Chronic pain affects one in four adults worldwide, and diagnosis currently relies on self-reported verbal pain assessments. Reliable and useful assessment of pain are crucial to the diagnosis and effective management of pain. Therefore, the development of objective biomarkers can revolutionize our ability to understand and treat pain. Biomarkers that demonstrate disease mechanisms are particularly useful, as they are more likely to be reproducible across distinct populations, and may guide therapies.

Online monitoring and entrainment of sleep spindles can provide additional benefits, as experimental evidence has suggested that spindle density predicts the effect of prior knowledge on memory consolidation. Sleep disorders or disturbances are important symptoms in many neurological or neuropsychiatric disorders. Characterization of sleep spindles (e.g., oscillatory frequency, spindle density, duration) can be used as an important biomarker related to brain health, or for early detection of neurodegenerative disorders such as mild cognitive impairment (MCI) and Alzheimer's disease, to predict stress and schizophrenia, or to provide a diagnostic and/or therapeutic target for treatment of pain.

SUMMARY OF THE INVENTION

One exemplary embodiment of the present invention relates to a method for administering stimulations to a sleeping subject. The method comprises (i) obtaining brain wave data generated based on brain wave activity of the subject over a predetermined time frame ($T_W$), (ii) determining a spectral power ratio of a spindle band to delta and theta bands of the brain wave data at a time within the predetermined time frame, and (iii) inputting the spectral power ratio and the brain wave data to a pretrained deep neural network to generate a probability score that sleep spindles are being detected in the brain wave activity. The brain wave data may be EEG data. In particular, the brain wave data may be generated from a single channel EEG. In some embodiments, the spectral power ratio may be obtained at the time $T_W/2$. The pretrained deep neural network may be trained based on at least one set of input data and corresponding output data. The input data may comprise reference brain wave data and the output data corresponding to a determination of presence or absence of sleep spindles based on the input data. The deep neural network may comprise a convolutional neural network followed sequentially by a recurrent neural network. The method also comprises (iv) continuously repeating steps (i) to (iii), as discussed above, and determining a presence of sleep spindles is detected when the probability score is above a predetermined threshold score over a predetermined threshold period of time. The method may further comprise (v) administering a brain stimulation to the subject when the presence of sleep spindles is detected. The brain stimulation may comprise either acoustic stimulation or non-invasive transcranial brain stimulation. In particular, the brain stimulation may be an acoustic stimulation configured to enhance sleep spindles or boost memory consolidation, without waking the subject.

In another aspect of the invention, a device for detection of sleep spindles in a subject is provided. The device may comprise a sensor configured to generate brain wave data corresponding to brain wave activity of the subject. The device may also comprise a processing arrangement operably connected to the sensor and configured to (i) obtain the brain wave from the sensor over a predetermined time frame, (ii) determine a spectral power ratio of a spindle band to delta and theta bands of the brain wave data at a time within the predetermined time frame, (iii) input the spectral power ratio and the brain wave data to a pretrained deep neural network to generate a probability score that sleep spindles are being detected in the brain wave activity, and (iv) continuously repeating (i) to (iii) and determining a presence of sleep spindles is detected when the probability score is above a predetermined threshold score over a predetermined threshold period of time. The pretrained deep neural network may be trained based on at least one set of input/output data samples. The input data may comprise reference brain wave data and the output data corresponding to a determination of presence or absence of sleep spindles based on the input data.

In a further aspect of the invention, a method for detecting chronic pain in a subject is provided. The method comprises (i) obtaining brain wave data generated based on brain wave activity of the subject over a predetermined time frame ($T_W$) during sleep, and (ii) determining a spectral power ratio of a spindle band to delta and theta bands of the brain wave data at a time within the predetermined time frame $T_W$. The method also comprises (iii) inputting the spectral power ratio and the brain wave data to a pretrained deep neural network to generate a probability score that sleep spindles are being detected in the brain wave activity. The pretrained deep neural network is trained based on at least one set of input data and corresponding output data. The input data comprises reference brain wave data and the output data corresponding to a determination of presence or absence of sleep spindles based on the input data. The method also comprises (iv) continuously repeating steps (i) to (iii) and determining a presence of sleep spindles is detected when the probability score is above a predetermined threshold score over a predetermined threshold period of time, and quantifying a severity of pain based on density of sleep spindles detected in steps (i) to (iv). The method may further comprise the step of (vi) administering a brain stimulation to the subject based on the severity of pain.

These and other aspects of the invention will become apparent to those skilled in the art after a reading of the following detailed description of the invention, including the figures and appended claims.

BRIEF DESCRIPTION OF THE FIGURES

FIGS. 4a through 17b show experimental data obtained according to Example I described in the present application.

DETAILED DESCRIPTION

Spindles provide an important signature for N2-stage sleep. In human sleep labs, spindle detection requires manual annotation by sleep experts, a resource-intensive task that is time consuming and subject to inter-rater variability. In animal sleep research, there are no publicly available datasets with expert-annotated spindles. Additionally, there may be great variability in spindle characteristics across different brain areas (e.g., hippocampus, thalamus, and neocortex) and recording tools (e.g., surface or intracortical EEG). The majority of work on automatic spindle detection is geared towards off-line applications for specific cohorts, which may rely on various techniques, including constant or adaptive thresholds, matching pursuit, time-frequency transform, decision tree and low-rank optimization. Although a few spindle detection algorithms have been adapted for online applications, their detection latencies have not been fully investigated. Therefore, their flexibility and detection latency for real-time brain-machine interface (BMI) applications requiring spindle-triggered closed-loop auditory or electrical stimulation remains untested. The latency consideration is critical because the timing of closed-loop stimulation affects targeted memory reactivation (TMR), in that acoustic stimulation has been shown to be most efficient when delivered at the descending phase of SO down state or during the transition from cortical down states to up states. Furthermore, since fast (13-16 Hz) or slow (9-13 Hz) spindles may occur during different phases of SO (half cycle: 0.5-1 s) or cortical (up vs. down) state and they may have differential roles in memory consolidation, a spindle detection latency longer than 350 ms may completely shift the SO phase during stimulation.

An important task of sleep studies in human and animal research is to detect sleep spindles—a physiological signature of stage-2 non-rapid-eye-movement (NREM) sleep. Sleep spindles play important roles in memory consolidation, sensory gating and neuronal development during sleep. The challenge of studying sleep spindles is the labor-intensive process of spindle identification and characterization. However, with recent advances in automated detection of sleep spindles using neural network algorithms, it is possible to study sleep spindle activity as a possible biomarker for certain health states.

Figure 1:
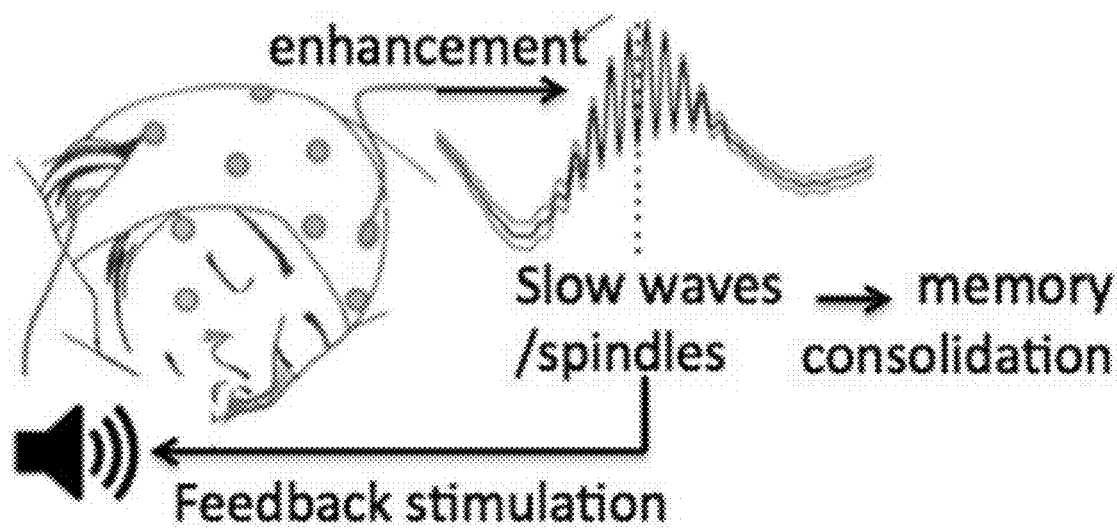
FIG. 1 shows an exemplary embodiment of a method for detecting slow waves and/or sleep spindles in order to provide feedback stimulation to a subject to enhance sleep spindles and/or boost memory consolidation of motor and cognitive tasks.

Automatic sleep spindle detection with reliable accuracy and quickest detection speed is important for real-time closed-loop brain machine interface (BMI) applications. In addition, sleep spindles can be used as a biomarker and for early detection of neurodegenerative disorders, therefore monitoring of sleep spindles in night or day-time sleep may provide valuable neurofeedback for potential therapeutic treatment, combined with acoustic stimulation or non-invasive transcranial brain stimulation. It is believed that spindle-triggered auditory or brain stimulations could enhance sleep spindles and further boost memory consolidation of motor and cognitive tasks. In these real-time closed-loop applications, speed (low latency) and accuracy (high sensitivity and specificity) are the key factors. (See FIG. 1).

Figure 2:
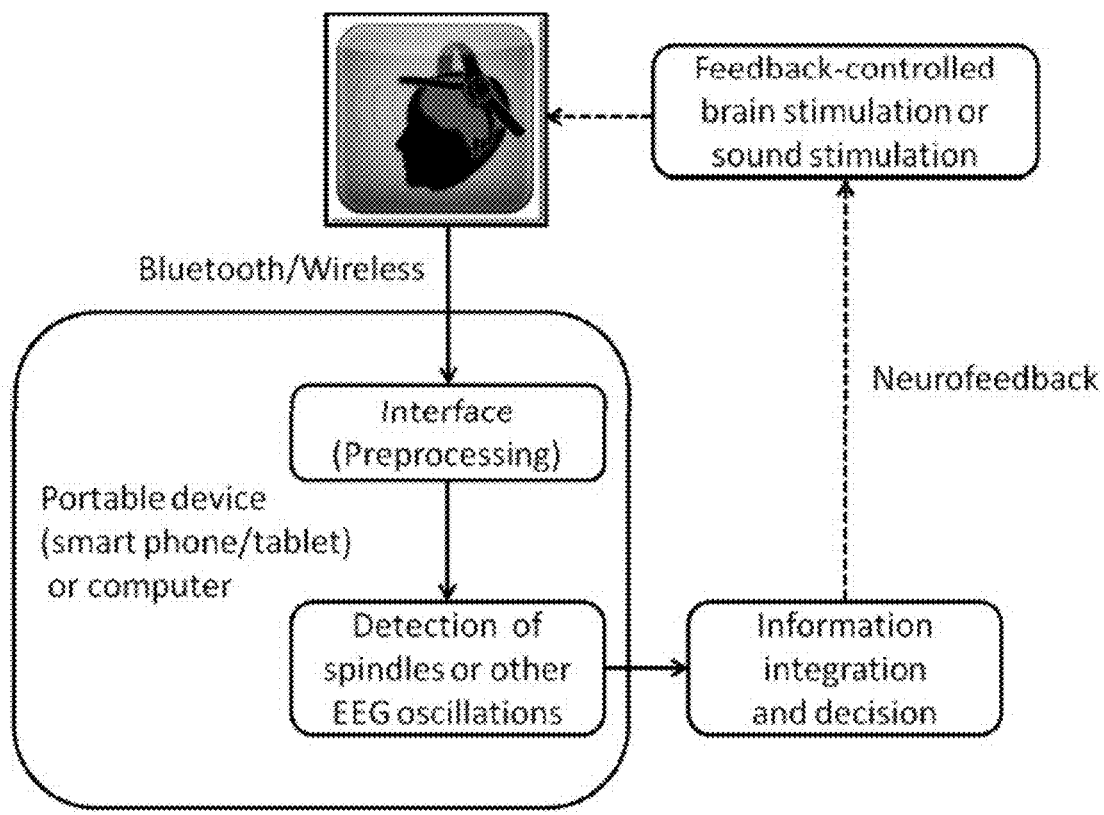
FIG. 2 shows an exemplary embodiment of a system for detecting subject EEG oscillations for detection of sleep spindles.
Figure 3A:
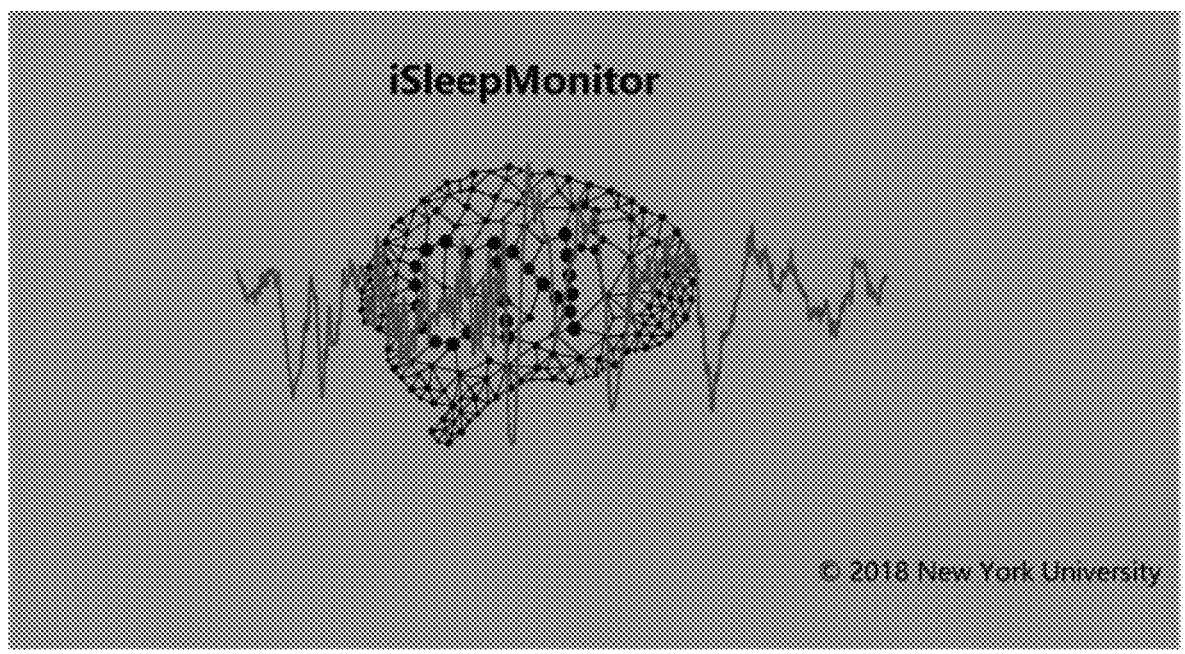
FIGS. 3a and 3b show exemplary embodiments of user interfaces for a system for detecting subject EEG oscillations for detection of sleep spindles.
Figure 3B:
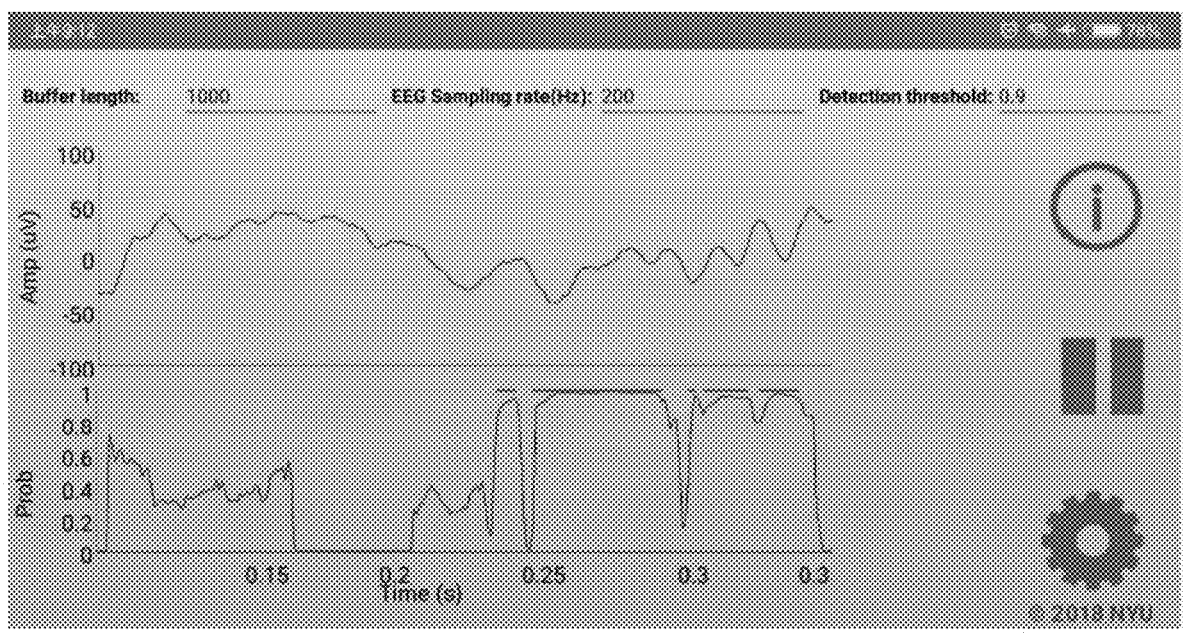

The system and method described in the present application for detecting human or animal EEG oscillations is believed to be superior to other available products in terms of lower latency and higher accuracy (lower false discovery rate). The system may work robustly under various EEG sampling frequencies (important for portable device based on lower sampling frequency). An exemplary embodiment of the system is shown in FIG. 2. Exemplary embodiments of the system have been tested on an Android smartphone and integrated with closed-loop feedback-controlled sound stimulation and wireless EEG data acquisition (through Bluetooth). FIGS. 3a and 3b show exemplary embodiments of user interfaces for a system for detecting subject EEG oscillations for detection of sleep spindles. In particular, the exemplary embodiments shown in FIGS. 3a and 3b are exemplary user interfaces on an Android smartphone. Furthermore, the system may detect or identify other EEG patterns during wakeful states, such as monitoring fatigue or sleepiness during driving, assessment of attention and decision-making.

In one exemplary embodiment, the method described in the present application may be directed to a method for detecting a sleep spindle in a patient. The method may further include administering stimulation to the subject in real-time or near real-time (e.g., have a latency of 350 ms or less, or having a latency from 150 to 350 ms) to improve sleep and/or enhance sleep spindles in the patient. The method includes a first step of obtaining brain wave data generated based on brain wave activity of the subject over a predetermined time frame ($T_W$). The brain wave data may be EEG data. In particular, the brain wave data may be generated from a single channel EEG. Alternatively, the brain wave data may be multi-channeled EEG data. The method further includes obtaining at least one feature from the brain wave data for further analysis with a pretrained neural network. In particular, the feature may be a spectral power ratio of a spindle band (e.g., EEG data at 9-16 Hz) to delta and theta bands (e.g., EEG data at 2-8 Hz) of the brain wave data at a time within the predetermined time frame ($T_W$), particularly, at a time $T_W/2$. The pretrained neural network may be a deep neural network for comparing the feature(s) extracted from the brain wave data to a set of reference data. The deep neural network may comprise a convolutional neural network (CNN) followed sequentially by a recurrent neural network (RNN). For example, the CNN may be used to learn various features from the set of reference data and the features may be further passed to the RNN to discover temporal patterns within the CNN features. The pretrained deep neural network may be trained based on at least one set of input data and corresponding output data. The input data may comprise reference brain wave data and the output data corresponding to a determination of presence or absence of sleep spindles based on the input data. For example, the reference brain wave data may be analyzed by at least one expert identifying the occurrence of sleep spindles. The brain wave data recorded from the patient, and the corresponding features, including the spectral power ratio, may be inputted into the pre-trained neural network to generate a quantitative value relating to the detection of sleep spindles, e.g., a probability score that sleep spindles are being detected in the brain wave activity. The method may determine that a presence of sleep spindles is detected when the probability score is above a predetermined threshold score over a predetermined threshold period of time. The method may continue by shifting the predetermined time frame ($T_W$) further down a time line for a period of time and repeating the above acquisition and analysis steps using a pretrained neural network to determine a presence of sleep spindles. The method may further comprise administering a brain stimulation to the subject when the presence of sleep spindles is detected. In particular, the brain stimulation may be administered in real time or near real-time such that the brain stimulation is delivered at the descending phase of SO down state or during the transition from cortical down states to up states in the patient. The brain stimulation may comprise either acoustic stimulation or non-invasive transcranial brain stimulation. In particular, the brain stimulation may be an acoustic stimulation configured to enhance sleep spindles or boost memory consolidation, without waking the subject. For example, the brain stimulation may be a low frequency, rhythmic acoustic stimulation (e.g., pink noise). More particularly, the brain stimulation is an acoustic stimulation, the acoustic stimulation being random pink noise based on a Gaussian random distribution. Further details for a method for detecting a sleep spindle and administering a brain stimulation in response is provided below in Example I.

The system and method described herein is believed to provide an improved sleep spindle detection method that is faster (provides reduced latency) compared to other previous methods. Notably, our spindle detection method can work well based on single EEG channel. In addition, we focus on optimized (timing/duration/frequency) acoustic stimulation for enhancing spindles. Further, the present application also includes portable devices (e.g., mobile phones) that accommodate such application in home or clinical monitoring. The present application also contemplates a system/portable device or apparatus to combine spindle detection (based on an advanced methods) and acoustic stimulation, targeted on human/animal sleep recording. On the technology side, the method may be implemented as software (e.g., C/C++, Java) for mobile devices for achieving these functions. In an exemplary embodiment, customized hardware (e.g., wearable EEG sensors) may also be constructed to be used in conjunction with the software to allow wireless data acquisition.

There is a growing need in the e-health monitoring market, and sleep spindles are believed to be useful as biomarkers for Alzheimer's disease, schizophrenia and/or pain. The system described herein may be used for sleep monitoring at home, and can be integrated with other available systems for improving sleep or enhancing sleep spindles for healthy adults and patients. For example, the system may provide real-time detection of sleep spindles (based on single EEG channel) and/or feedback-triggered acoustic stimulation for spindle enhancement. The method incorporated into the system may provide additional benefits, such as superior performance in real-time applications, e.g., improving the detection latency compared to other methods for identifying sleep spindles. Furthermore, it is contemplated that the system of the present application may be embodied, for example, in a portable device (e.g., smartphone) that allows easy sleep monitoring at home or in a sleep laboratory.

Spindle events have been implicated in memory consolidation and synaptic plasticity processes during NREM sleep. Detection accuracy and latency in automatic spindle detection are critical for real-time applications. Example I provides a novel deep learning strategy (SpindleNet) to detect sleep spindles based on a single EEG channel. While the majority of automatic spindle detection methods are used for off-line applications, our method is well suited for online closed-loop experiments. Compared with other published spindle detection methods, SpindleNet achieves superior detection accuracy and speed, as demonstrated by comparing to two publicly available expert-validated EEG sleep spindle datasets. Our real-time detection of spindle onset achieves detection latencies of 150-350 ms (~2-3 spindle cycles) and retains good performance under low EEG sampling frequencies and low signal-to-noise ratios. SpindleNet has good generalization across different sleep datasets from various subject groups of different ages (children/adult/elderly) and species (human/rat). Overall, SpindleNet is ultra-fast and scalable to multichannel EEG recordings, with an accuracy level comparable to human experts, making it appealing for long-term sleep monitoring and closed-loop neuroscience experiments.

Pain is known to disrupt sleep patterns, and disturbances in sleep can further worsen pain symptoms. Sleep spindles occur during slow wave sleep have established effects on sensory and affective processing in mammals. A number of chronic neuropsychiatric conditions, meanwhile, are known to alter sleep spindle density. The effect of persistent pain on sleep spindle waves, however, remains unknown, and studies of sleep spindles are challenging due to long period of monitoring and data analysis. Utilizing automated sleep spindle detection algorithms built on deep learning, as described above, we can monitor the effect of pain states on sleep spindle activity. For example, detection of sleep spindles using a pretrained deep neural network, as described above, may also be useful in detecting chronic pain. In particular, a decrease in sleep spindle density detected may be determined to correspond to a presence of pain, in particular, chronic pain. Furthermore, the sleep spindle density may be a quantitative value used to determine and/or quantify a severity of pain. Brain stimulation, in particular, acoustic stimulation similar to that described above, may be administered to the patient upon detection of a sleep spindle for treating or ameliorating chronic pain. The brain stimulation may be an acoustic stimulation that is suitably selected for reducing chronic pain by stimulating elevation of spindle density in the patient.

In another exemplary embodiment, a method for detecting chronic pain in a subject is provided. The method includes similar steps for obtaining brain wave data and analyzing the brain wave data with a pretrained neural network to identify the presence of sleep spindles as described above. The method also further includes quantifying a severity of pain based on density of sleep spindles detected. The method may also further include a step for administering a brain stimulation to the subject based on the severity of pain. Further details for a method for detecting, ameliorating or treating pain, in particular chronic pain is provided below in Example II.

In Example II, we apply the deep learning method of Example I, known as SpindleNet, to characterize sleep spindle activity in chronic pain-treated rats. Our results indicate that sleep spindle density is decreased in a model of chronic inflammatory pain. Further, we show that pink noise, an established method to increase spindle density, can effectively decrease pain sensitivity in this animal model.

Those skilled in the art will understand that the exemplary embodiments described herein may be implemented in any number of manners, including as a separate software module, as a combination of hardware and software, etc. For example, the exemplary methods may be embodiment in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed above. The at least one of the plurality of processor cores or a separate processor may be incorporated in or may communicate with any suitable electronic device, for example, a mobile computing device, a smart phone, a computing tablet, a computing device, etc.

For example, the exemplary methods may be embodied in an exemplary system comprising a processing arrangement. For example, an exemplary method described herein may be performed entirely or in part by the processing arrangement. Such processing/computing arrangement may be, e.g., entirely or a part of, or include, but not limited to, a computer/processor that can include, e.g., one or more microprocessors, and use instructions stored on a computer-accessible medium (e.g., RAM, ROM, hard drive, or other storage device). A computer-accessible medium (e.g., as described herein, a storage device such as a hard disk, floppy disk, memory stick, CD-ROM, RAM, ROM, etc., or a collection thereof) may also be provided (e.g., in communication with the processing arrangement) in the system. The computer-accessible medium may be a non-transitory computer-accessible medium. The computer-accessible medium can contain executable instructions thereon. In addition or alternatively, a storage arrangement can be provided separately from the computer-accessible medium, which can provide the instructions to the processing arrangement so as to configure the processing arrangement to execute certain exemplary procedures, processes and methods.

Example I

Machine learning has recently emerged as a powerful tool in big data analysis. Deep learning algorithms, powered by scalable computational resources and large datasets, have shown superior performances in a wide range of tasks, including playing the game of Go, large-scale image and speech recognition, sleep staging, EEG-based prediction, clinical monitoring, and medical image analysis. However, deep learning has not been fully investigated in the context of automatic spindle detection; spatiotemporal features have not been optimized for this detection task. To improve detection latency and accuracy of sleep spindles, we have developed a deep neural network (DNN) approach, termed as SpindleNet, to learn the complex nonlinear features and spectrotemporal structures of sleep spindles. Based on two public annotated sleep spindle datasets, we construct a large number (order of millions) of labeled examples and train the DNN using advanced machine-learning techniques. Since annotated spindles are rare, we propose a transfer learning method in combination with synthetic spindles through computer simulations, to extend spindle detection to a wide variety of datasets (patient populations, noninvasive and invasive EEG, human and animal). Transfer learning allows us to store knowledge gained from solving one problem with sufficient existing labeled data in one domain, and apply it to a different but related problem in another domain. We validate the robustness of our transfer learning method on cross-subject, cross-age/health group, and cross-species (human-to-animal) scenarios.

FIG. 4. SpindleNet: deep neural network (DNN) architecture used for spindle detection. a, Overall architecture of the network. The input to subnetwork 1 and 2 consists of raw EEG signal and the envelope of bandpass filtered (9-16 Hz) EEG signal, respectively. The power features that are directly input to the fully connected layer consist of the ratio of the average power of spindle-band frequencies (9-16 Hz) to that of lower frequencies (2-8 Hz) and the instantaneous power of all frequencies from (2-16 Hz). The convolutional neural network (CNN) acts as a temporal feature extractor. The features learned by the CNN are further passed to a recurrent neural network (RNN) that is intendent to discover temporal patterns within the CNN features. The RNN implementation consists of a single-layer long short-term memory (LSTM). The output of the RNN (from 50 time steps) of subnetwork 1 is combined with the output of RNN from the subnetwork 2 and the power features using a fully connected layer. Output of this layer (of length 50) is further processed by a softmax activation function that produces a probability output (spindle vs non-spindle). b, Detailed architecture of the 5-layer CNN. The input is processed by a total of 5 layers. Every layer consists of 40 1D filters of size 7×1, followed by max-pooling with kernel size 5×1. For 250-ms EEG with 200 Hz sampling frequency, the size of input is 50. Batch size is set to B=20. c, A set of 7×1 learned receptive fields (RFs) from the first-layer CNN filters upon completion of training. The 1D filters share a resemblance to the shape of half cycle of spindle oscillation. d, The learning convergence curve on training and validation data. e, The change of detection accuracy with respect to two learning hyperparameters: learning rate and drop-out rate. f, The change of AUROC statistic with respect to the learning rate and drop-out rate.

FIG. 5. Statistics of MASS dataset. a, Statistics of NREM duration (min) on 19 human subjects. b-d, Statistics of annotated spindle number (b), onset time difference between two experts (c) and amplitude standard deviation (d). In panel c, n/a represents the condition only one expert's annotation was available; the onset time difference among 15 subjects were 0.167±0.007 s (mean±SEM). e-h, In subject #1, statistics discrepancy between two experts on the commonly annotated sleep spindles' normalized power (e), duration (f), power ratio (g) and difference between two experts (Expert 2-Expert 1) on the spindle onset and duration (h).

FIG. 6. Results on online sleep spindle detection. a, A representative snapshot of EEG trace (during stage-2 NREM sleep) with human marked sleep spindles (in red). b, Associated EEG multi-taper spectrogram (1 s moving window, 5 ms step size). Arrows in panels a and b denote a potentially unlabeled spindle by two experts, which was detected by SpindleNet. c, Softmax probability output (blue) and the final hard decision (red, probability threshold 0.9) for online spindle detection. d, Representative EEG traces (blue) during stage-3 NREM sleep that demonstrate coupling between slow wave (0.5-4 Hz, black trace) and spindles (marked in red). In these two examples, fast (13-16 Hz) sleep spindles tend to occur in the ascending phase of SO cycle (or be coordinated with depolarizing cortical up state), whereas slow (9-12 Hz) spindles tend to occur in the descending phase of SO cycle, or during the transition from cortical down to up states. Note that a large latency in spindle detection may switch from the up ascending phase to the down descending phase of the SO. e, Summarized results (from 5-fold cross validation) of sensitivity, specificity, false discovery rate (FDR), F1-score and AUROC statistics in the MASS dataset (n=19 subjects). Error bar represents SEM. f, Summarized results of sensitivity, specificity, FDR, F1-score and AUROC statistics in the DREAM dataset (n=8 subjects), using SpindleNet trained from the MASS dataset without further fine tuning as well as with fine-tuning using real and simulated spindles. Fine-tuning with real and simulated data further improved the performance. Error bar represents SEM. g, Results on spindle detection from the MASS dataset (n=19 subjects, error bar represents SEM) under various EEG sampling frequencies. Model 1: standard model trained with EEG signal with 200 Hz sampling rate; Models 2-4: models trained on down-sampled EEG signals at frequencies 100 Hz, 50 Hz, 34 Hz, respectively. In testing EEG signals with <200 Hz sampling frequency, we either up-sampled the signal and applied the standard model (Model 1), or applied the respective model for the sampling frequency. SpindleNet demonstrated robust performance across various sampling frequencies.

FIG. 7. Performance comparison between our method (SpindleNet) and the McSleep algorithm on two public sleep spindle datasets. a, Examples of sleep spindle detection where the McSleep algorithm detected a false event in the MASS dataset, whereas the softmax probability output (blue trace) from SpindleNet was below the detection threshold. b,c, Summarized performance on the MASS dataset (n=15 subjects, with annotations from two experts). *, $p<0.05$; **, $p<0.01$, unpaired t-test. d, Comparison of the kappa statistic between two methods, as well as between them and ground truth (GT). e-g, Similar to panels b-d, except for the DREAMS dataset (n=6 subjects, with annotations from two experts).

FIG. 8. Performance comparison between our method (SpindleNet) and McSleep on simulated spindle data with varying levels of signal-to-noise ratio (SNR). a, Sensitivity. b, Specificity. c, False discovery rate. d, F1-score. The Inf SNR denotes the noiseless condition. e, Histogram of detection latency in the noiseless condition. f, Mean detection latency of our proposed method with respect to the SNR. g, Spindle detection latency based on the AND and OR criteria. Error bar represents SEM (n=19 subjects).

FIG. 9. Left: The sensitivity of spindle detection improved with increasing training sample size (both tested on the same test data). Right: The F1-score of detection gradually increased with increasing training sample size.

FIG. 10. Construction of sleep spindle training examples from raw EEG traces. We used a 250-ms overlapping moving window (dashed and solid boxes) to construct positive and negative samples. Any EEG traces with ≥50% duration (i.e., 125 ms) coverage of the annotated spindle event (shaded period) was treated as a spindle (positive) example; everything else was a non-spindle (negative) example.

Figure 11A:
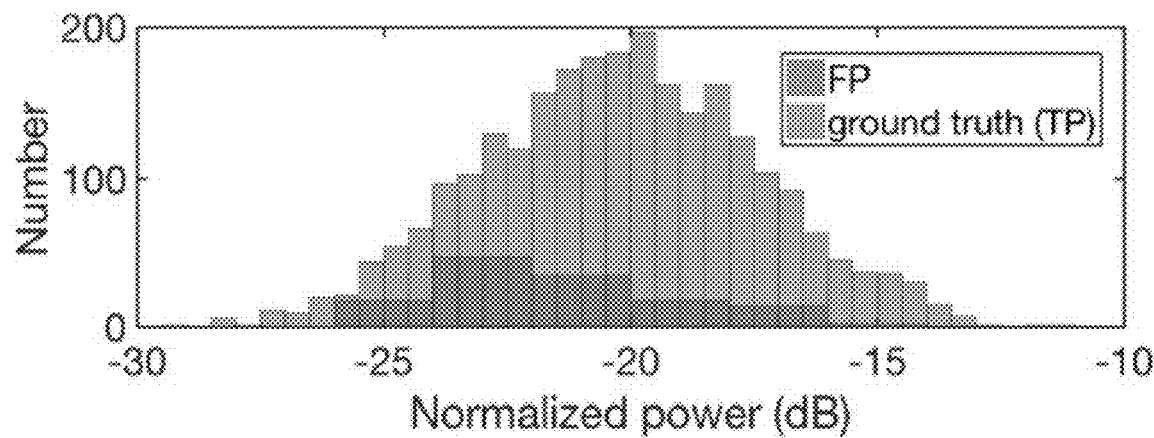
Figure 11B:
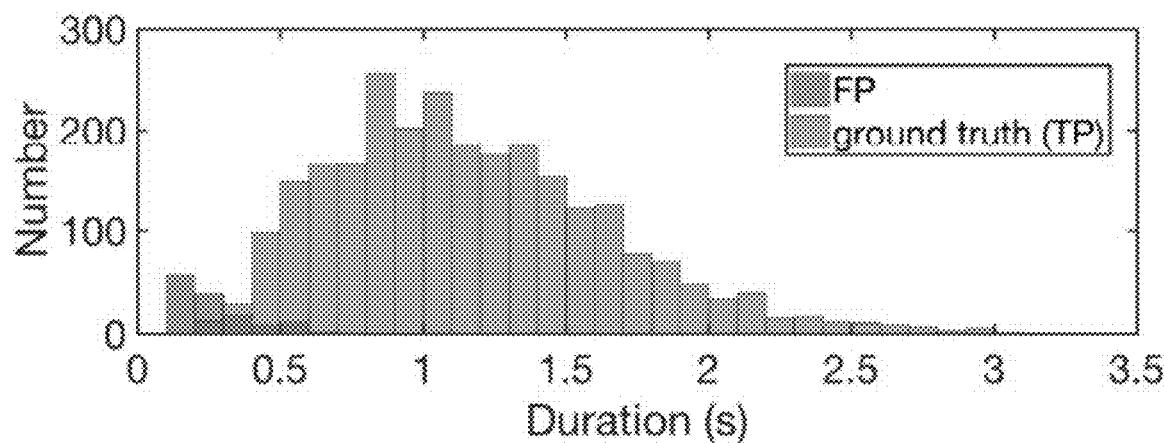

FIG. 11. Comparison of false positive (FP) detections with sleep spindle ground truth (TP). The normalized power (top) and duration (bottom) statistics are shown (from the MASS dataset).

Figure 12:
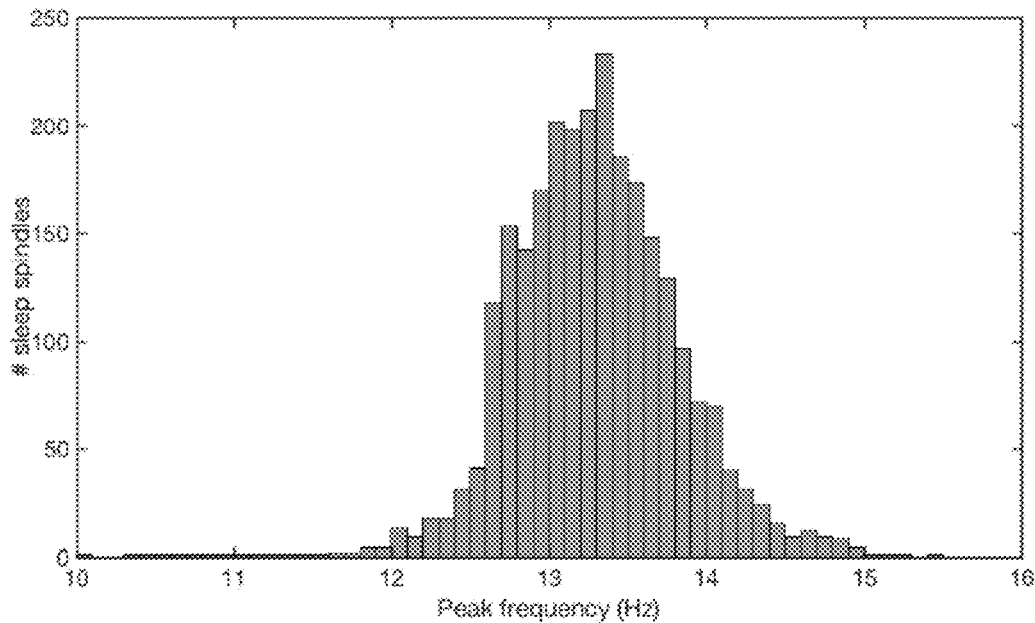

FIG. 12. The distribution of peak frequency of annotated sleep spindles during stage-2 NREM sleep. Note that in this example (Subject 1 of MASS dataset), the fast (13-16 Hz) spindles were more prevalent than slow (9-12 Hz) spindles.

Figure 13A:
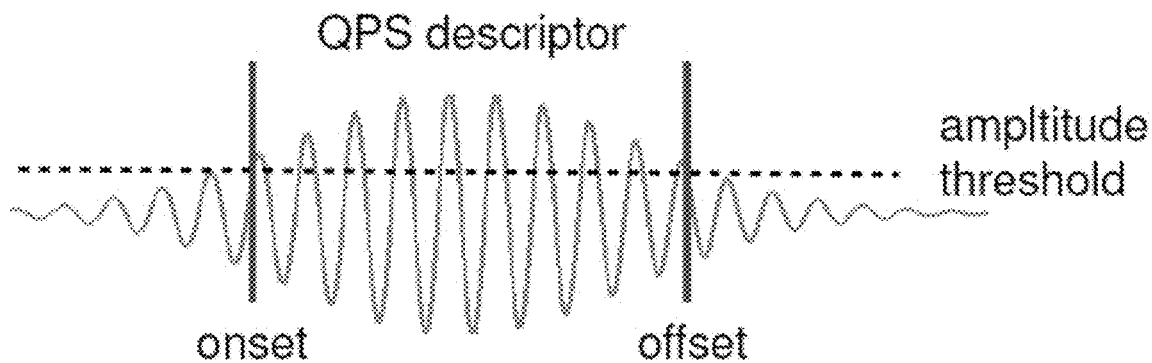
Figure 13B:
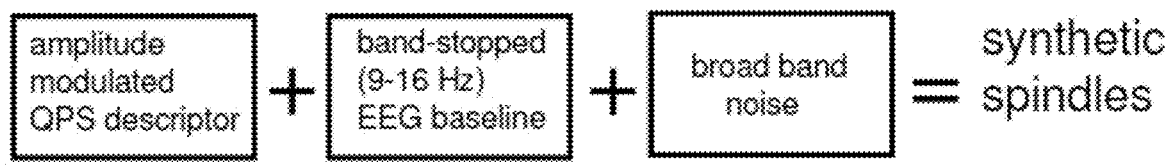

FIG. 13. Generation of synthetic spindles. a, An amplitude-modulated, quadratic parameter sinusoid (QPS) descriptor for spindles. The two vertical lines mark the onset and offset of spindles, which pass the threshold of 20% of peak amplitude. b, Schematic diagram of generating synthetized sleep spindles.

Figure 14:
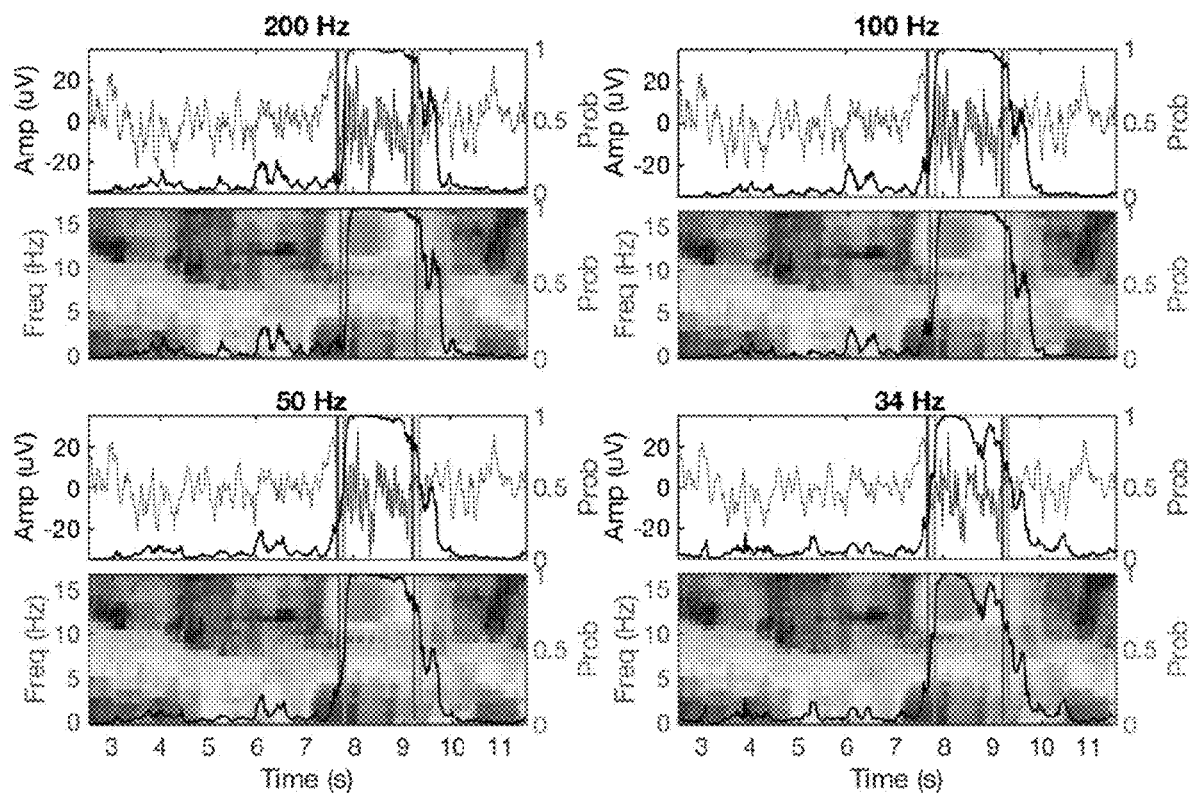

FIG. 14. Illustration of EEG traces and spectrograms with annotated (between two red vertical lines) and detected (marked by green vertical lines) sleep spindles at four different sampling frequencies. Black trace denotes the softmax probability output from SpindleNet. Despite the lower sampling rate and loss of fidelity in EEG spindles, SpindleNet detected the spindle onset reliably.

Figure 15:
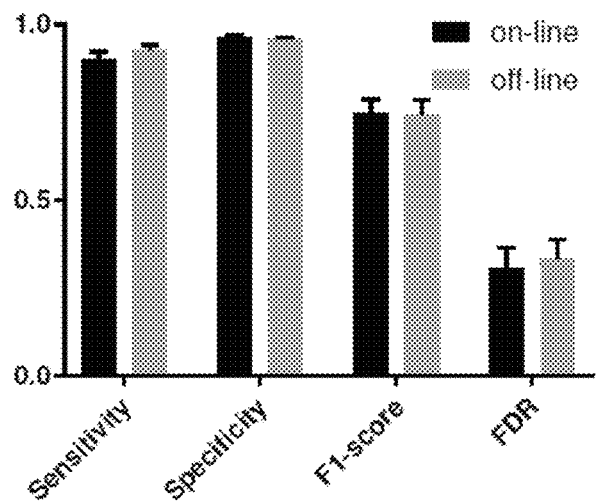

FIG. 15. Performance comparison of on-line vs off-line detection in SpindleNet. Error bar represents SEM (n=19 subjects, MASS dataset).

FIG. 16. Representative examples of sleep spindle detection from various sleep datasets. a, Children (CHAT). b, Elderly (MrOS). c, Epilepsy patient. d, Rat. e-f, Comparison of detected sleep spindle characteristics (frequency, duration and power) between our method (SpindleNet) and the McSleep algorithm.

Figure 17A:
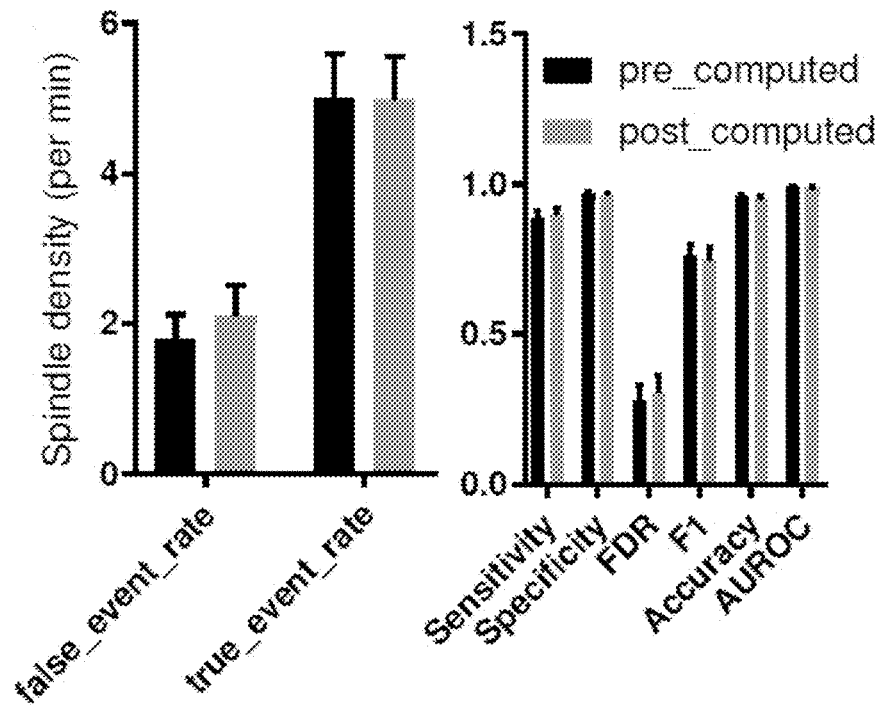
Figure 17B:
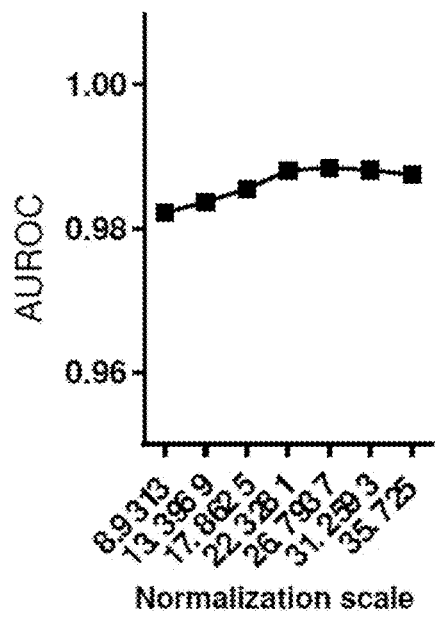

FIG. 17. Sleep spindle detection performance with respect to different normalization factors. a, False event rate and true event rate for pre and post computed normalization on the MASS dataset (n=19). b, Sensitivity, specificity, FDR, F1-score, accuracy and AUROC for pre and post-computed normalization on the MASS dataset (n=19). Pre-computed normalization is the average spindle standard deviation from the training set, whereas post-computed normalization is the average standard deviation from the testing set. c, Testing on the MASS subject #18 with various normalization scales in sleep EEG calibration.

Results

Overview

Figure 4A:
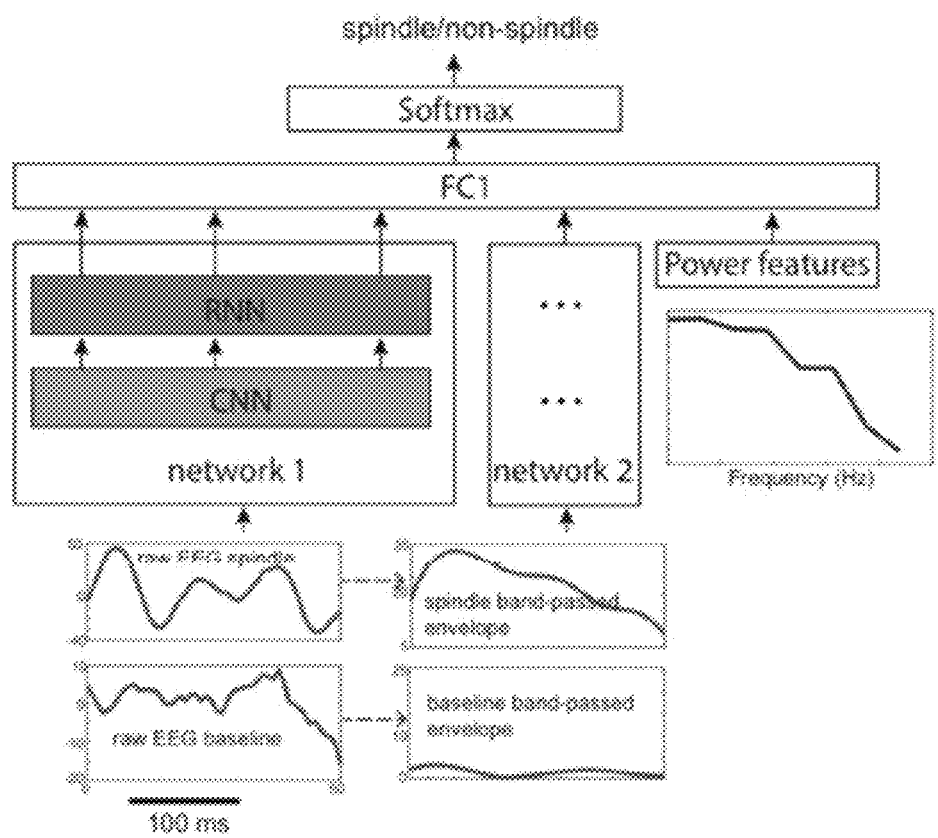
Figure 4B:
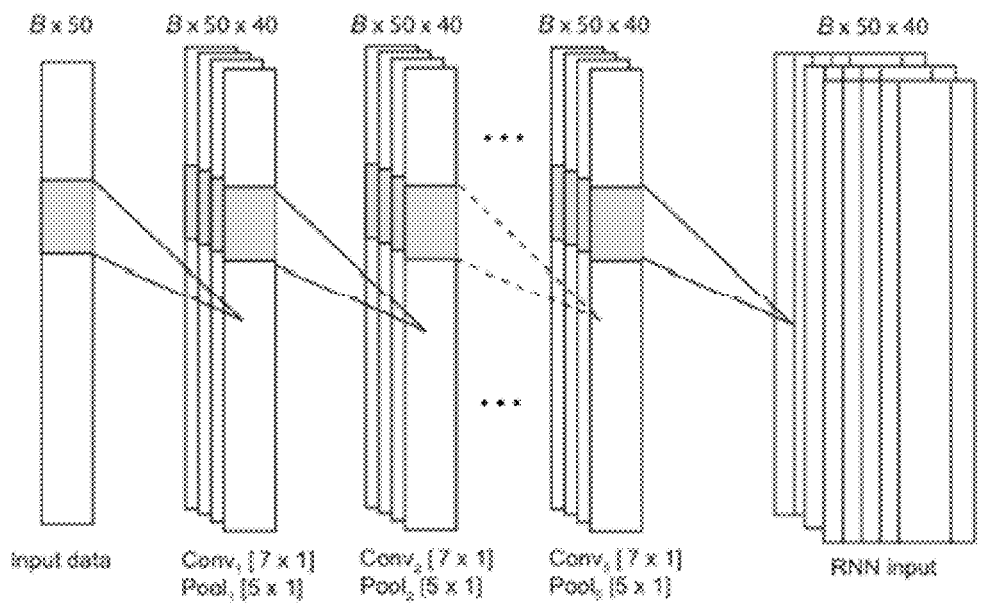

Two of the most widely used types of deep learning architectures are convolutional neural networks (CNNs) and recurrent neural networks (RNNs). We developed a DNN architecture that integrates a CNN with a RNN in a sequential structure (FIG. 4a). The CNN consists of 5 convolution layers (FIG. 4b). The input consists of i) a 1×50 (0.25 s×200 Hz) vector of EEG time series; ii) the envelope of the band-pass filtered (9-16 Hz) signals of the same length; and iii) EEG power features. The convolution operation consists of 40 one-dimensional (1D) temporal filters (vectors) of size 1×7, followed by exponential linear activation. The RNN consists of 100 long short-term memory (LSTM) cells, followed by one fully connected layer and one output layer with a softmax activation function.

Figure 4C:
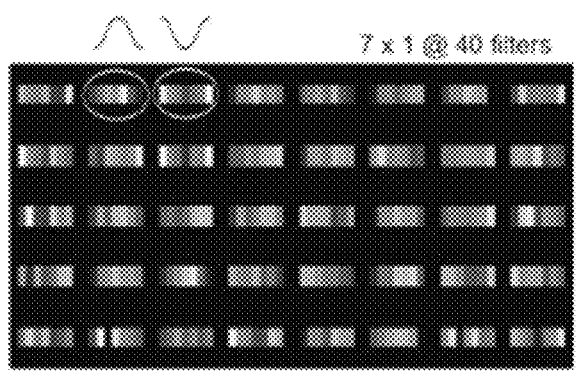
Figure 4D:
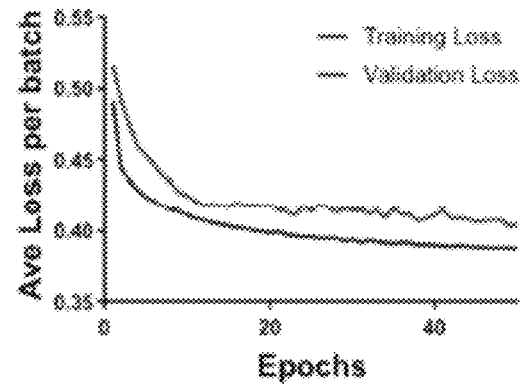
Figure 4E:
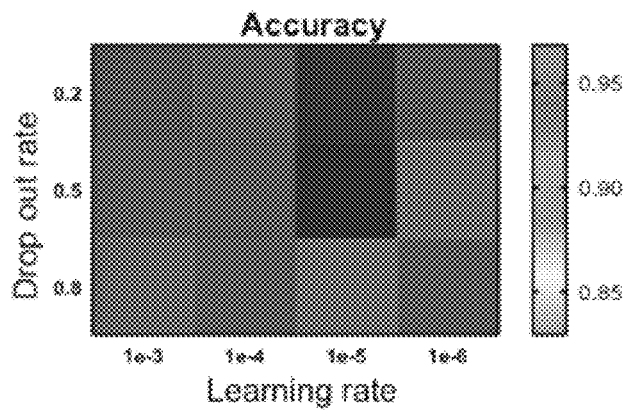
Figure 4F:
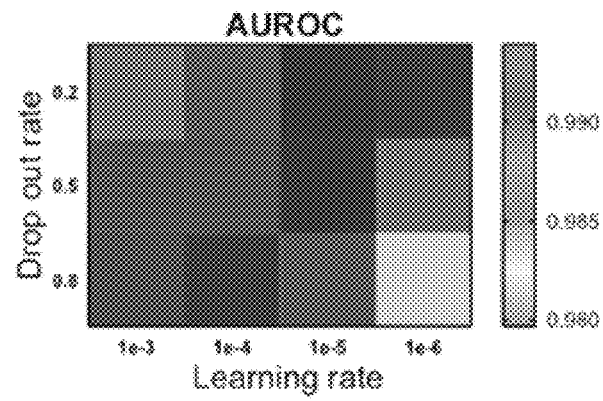

We constructed independent training and validation samples for sleep spindles from annotated human EEG recordings. Using discriminative supervised learning, we trained SpindleNet using a stochastic optimization algorithm. For each subject's recording, SpindleNet was trained on approximately 1-2 million experimental EEG traces in the time domain. Upon completion of training, we examined the receptive field (RF) representation of the learned convolution filters. The first-layer filters behaved as matched filters that showed temporal structure characterizing spindle oscillations (FIG. 4c). The second and higher-layer filters represented higher-order spectrotemporal features. During training, we monitored the convergence process based on training and validation loss functions to avoid overfitting (FIG. 4d), and the network size and hyperparameters were optimized using grid search method. However, the detection performance was robust to the exact choice of hyperparameters (FIG. 4e,f). Detection performance of deep learning depended on the size of training samples. Adding training samples gradually improved the accuracy of testing data until ultimately reaching the performance plateau (FIG. 9), indicating the importance of large-scale data in deep learning.

Among all annotated spindle events, there was inevitably an unknown level of label noise where two experts disagreed. We plotted the histograms of duration, power and power ratio statistics of annotated spindles produced by two human raters (FIG. 5). Differences in these statistics suggested subjective biases in human annotation.

Results on Two Annotated Human Sleep Datasets

We tested two public annotated sleep spindle datasets, which contained nocturnal sleep EEG recordings from healthy subjects (MASS) and from subjects with sleep pathologies (DREAMS). The training data were constructed from a subset of 19 healthy adult subjects from the MASS dataset. The NREM sleep duration and spindle statistics varied across subjects (FIG. 5a-d). In addition, there was a large variability in annotated spindle statistics between two human experts (FIG. 5e-h). We used an "OR" criterion from two experts to construct putative true positives (TPs) for spindles (FIG. 10). In addition, there were unlabeled spindle examples from two experts, which could nevertheless be detected by our method (see an example marked by arrows in FIG. 6a,b). Although sleep spindles were only annotated during N2 sleep in the MASS dataset, we were able to identify sleep spindles during N3-stage sleep, which are often temporally coupled with slow oscillations (FIG. 6d). Due to the lack of expert-identified spindles to provide ground truth, N3-stage spindle statistics were not used in the result assessment.

Figure 6A:
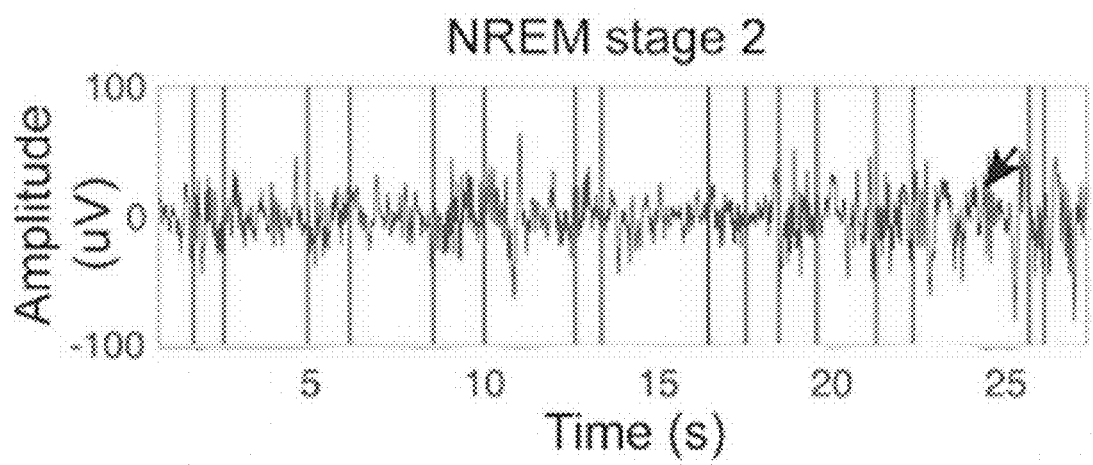
Figure 6B:
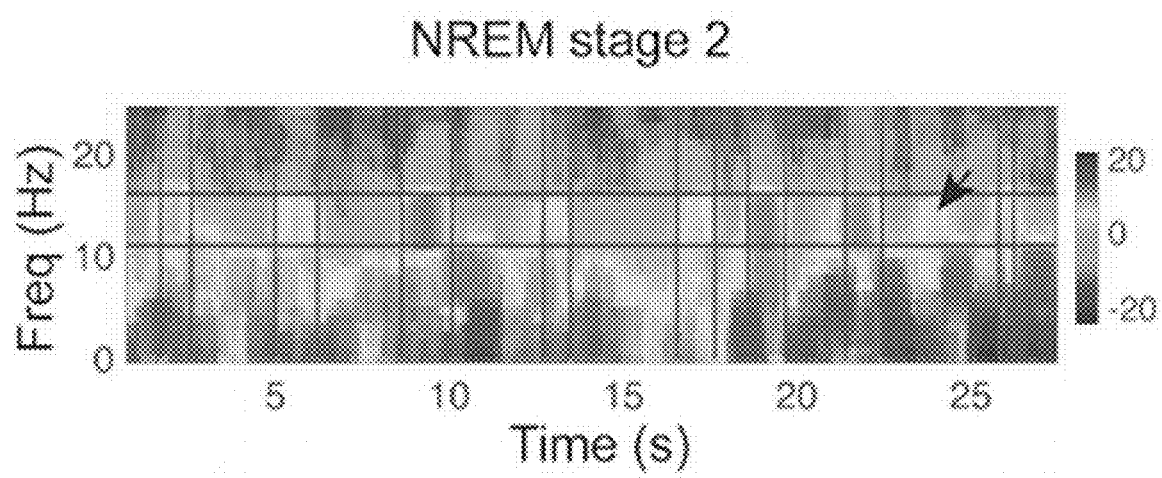
Figure 6C:
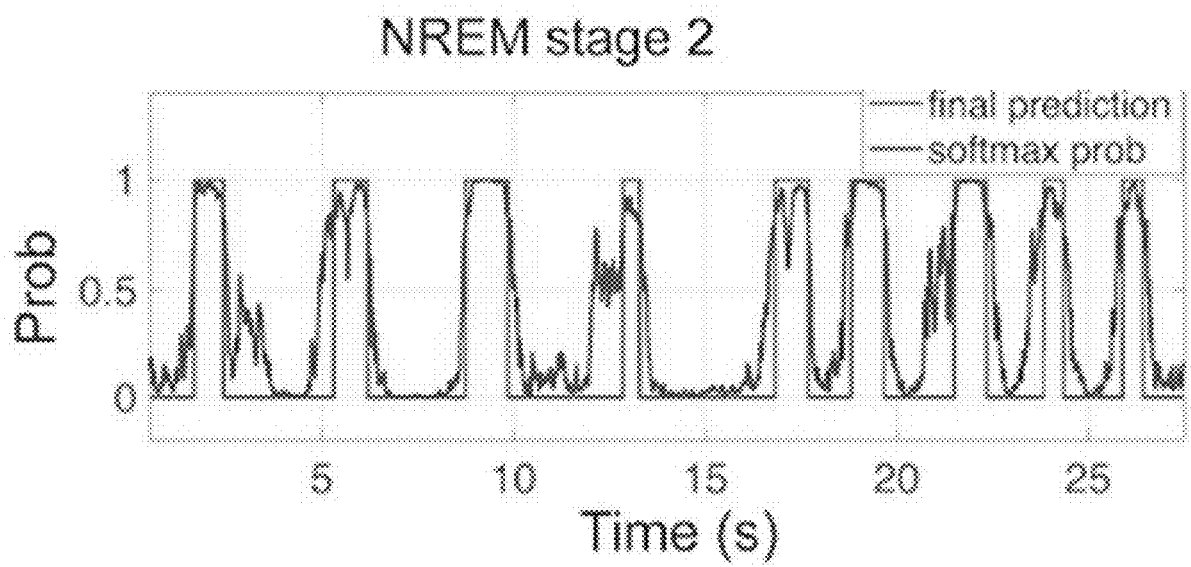
Figure 6D:
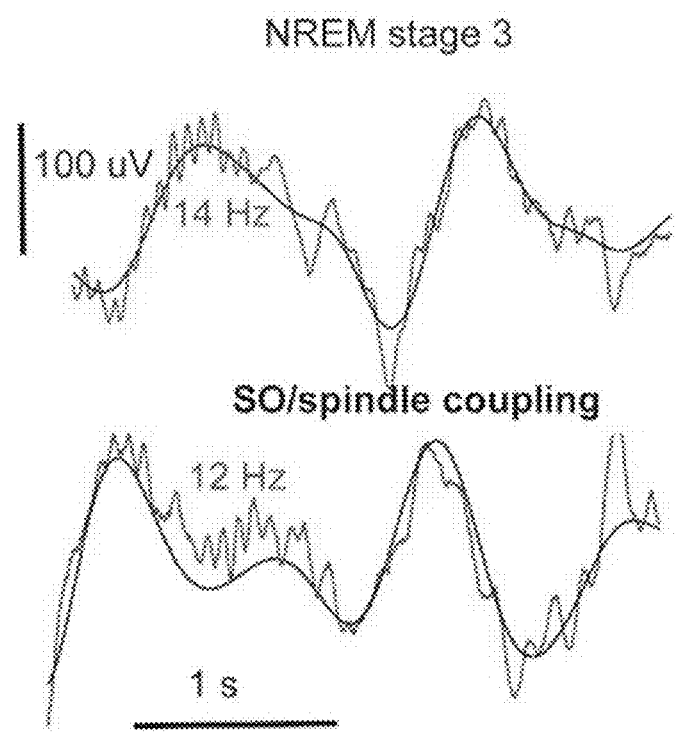
Figure 6E:
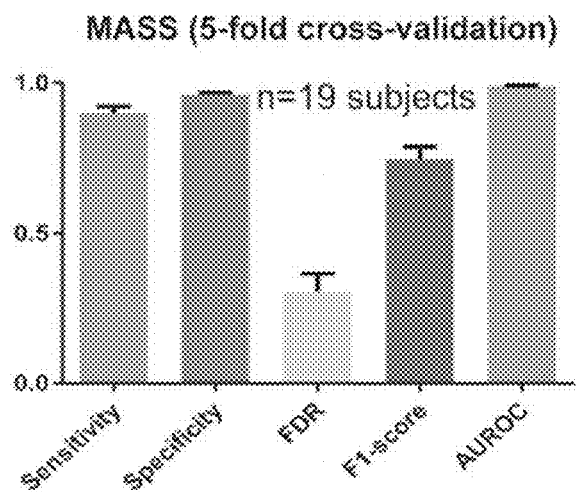
Figure 6F:
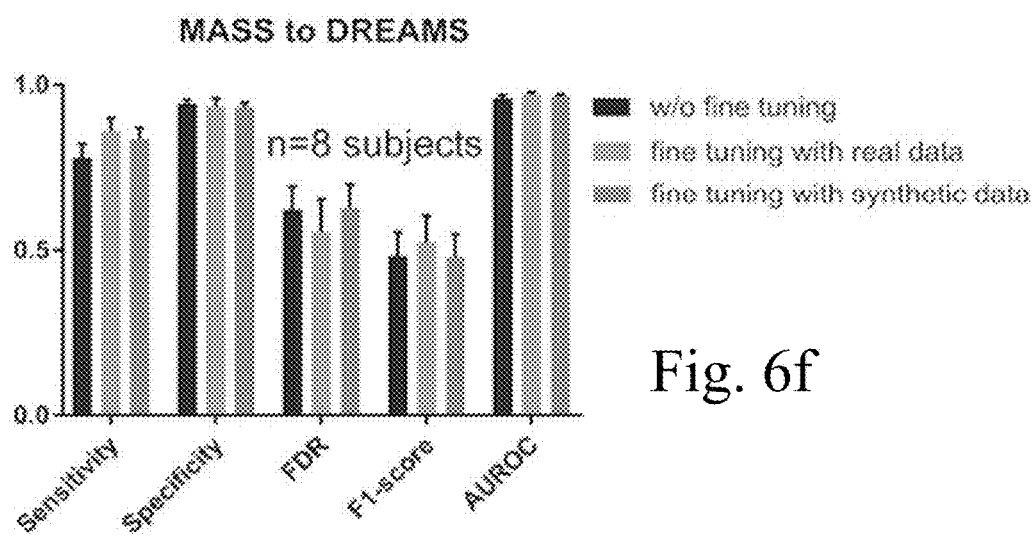

We first assessed the spindle detection performance based on the MASS dataset. We trained SpindleNet with the N2-stage sleep recordings using a 5-fold cross-validation scheme and computed sensitivity, specificity, false discovery rate (FDR), and F1-score (FIG. 6e). Among the subsets of 25,453 putative spindles (n=19 subjects), our method achieved sensitivity of 90.07±2.16%, specificity of 96.19±0.71%, FDR of 30.36±5.88%, F1-score of 0.75±0.05 and AUROC of 98.97±0.13% (mean±SEM). We also compared the statistics of false positive (FP) detections with that of the spindle TPs (ground truth) for duration and power, and found that these two sets were nearly inseparable in the overlapping feature space (FIG. 11), indicating the possibility that SpindleNet detected spindles that might be missed by experts. Among those putative spindles, we further computed their Fourier spectra and categorized them into fast (13-16 Hz) and slow (9-12 Hz) spindles. During N2 sleep, the occurrence distribution of fast and slow spindles varied (FIG. 12).

Next, we tested SpindleNet trained from the MASS dataset on the unseen DREAMS dataset. Despite the differences in spindle statistics between the two datasets, SpindleNet achieved good generalization (sensitivity, 77.85±4.28%; specificity, 94.2±1.26%; FDR, 61.96±7.39%; F1-score, 0.48±0.07; and AUROC, 95.97±0.96%) while testing on the DREAMS dataset (FIG. 6f, w/o fine tuning; referred to as baseline). To further improve the baseline performance, we fine-tuned SpindleNet using annotated spindles from the DREAMS dataset. As a result, the detection accuracy showed an improved trend for a small sample size (FIG. 6f, signed rank test: FDR, p=0.0547; F1-score, p=0.0547, sensitivity, p=0.25; n=8). Alternatively, we fine-tuned SpindleNet using simulated spindle samples (FIG. 13); and the detection results were also similar or slightly improved compared to the baseline. Overall, SpindleNet have demonstrated excellent generalization ability between human EEG sleep datasets, with varying health conditions and/or spindle statistics.

Figure 6G:
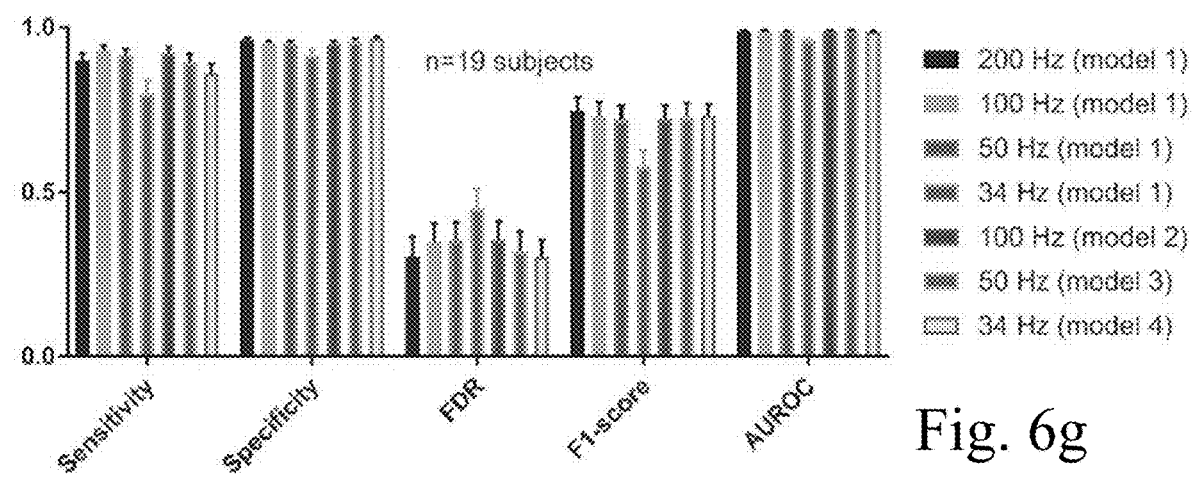

Furthermore, we investigated the robustness of SpindleNet with respect to the sampling frequency of EEG signals. We resampled EEG signals from the MASS dataset with lower sampling frequencies (100 Hz, 50 Hz and 34 Hz). As a result of down sampling, spindle detection may suffer from the loss of fidelity of EEG signals (FIG. 14). By default, the standard model trained with a sampling frequency of 200 Hz was termed as Model 1. By keeping the input duration (250 ms) unchanged, we retrained different network models under different EEG sampling frequencies (Models 2-4 for sampling frequencies of 100 Hz, 50 Hz, and 34 Hz, respectively) but with the same training sample size. During the testing phase, the EEG signals with lower sampling frequency were either first up-sampled to 200 Hz and then tested by Model 1 (ad hoc option 1), or directly tested by their respective reduced models (Models 2-4; option 2). Compared to the ad hoc option, option 2 produced comparable or slightly better performance (FIG. 6g). The difference between these two options was most pronounced in the lowest sampling frequency, where the sensitivity, FDR and F1-score statistics were significantly better in option 2 than in option 1 (signed rank test, sensitivity, p=0.0158; FDR, p<0.001; F1-score, p<0.001; n=19). This result suggested that SpindleNet was robust with respect to a wide range of sampling frequencies, and even performed well up to the Nyquist limit (twofold of the maximum spindle frequency of 16 Hz).

Comparison with Other Spindle Detection Methods

We compared SpindleNet with one recently published automatic spindle detection method known as the McSleep algorithm. We chose this algorithm because it has been tested on both the MASS and DREAMS datasets, and has been compared against other spindle detection methods.

Figure 7A:
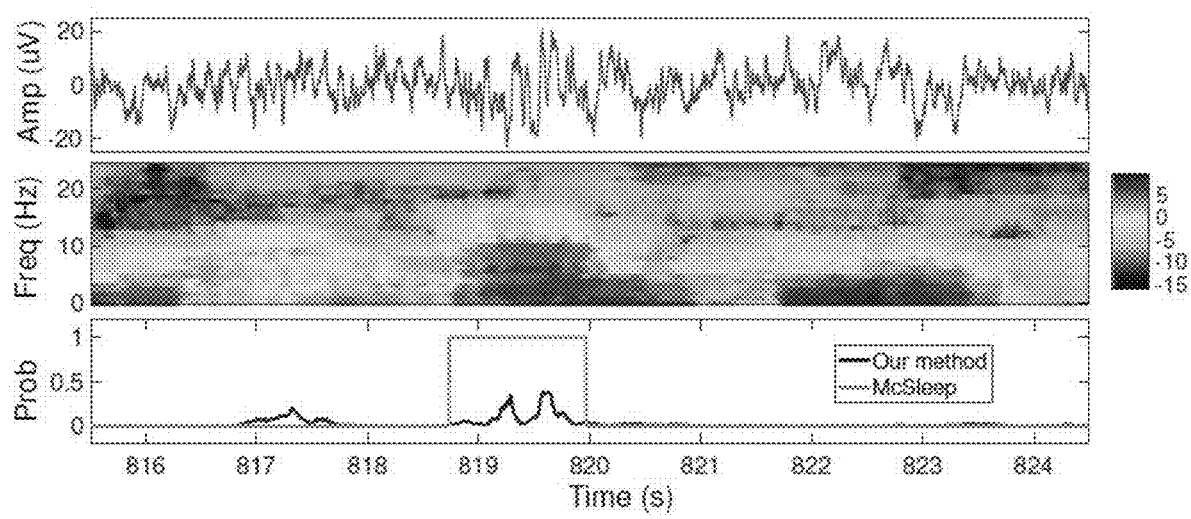
Figure 7B:
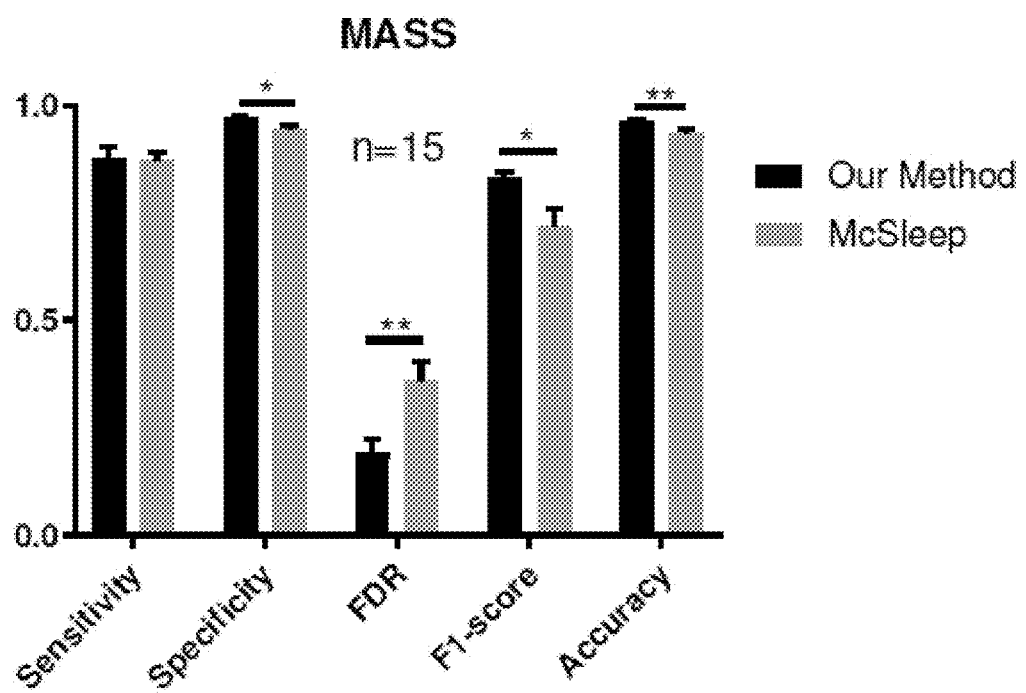

First, we selected the sleep spindle recordings with annotations from two human experts in both datasets (n=15 subjects for MASS and n=6 subjects for DREAMS). We ran the two detection methods and compared various performance indices (FIG. 7b-d). On the reduced MASS dataset (n=15 subjects), SpindleNet achieved specificity of 97.06±0.67% (McSleep: 94.49±0.77%, p=0.0183, unpaired t-test); FDR of 19.03±3.18% (McSleep: 35.71±4.6%, p=0.0061); F1 score of 0.83±0.02 (McSleep: 0.72±0.04, p=0.0124); accuracy of 96.08±0.44% (McSleep: 93.75±0.57%, p=0.003); and false event rate of 1.57±0.36 spindles/min (McSleep: 2.97±0.43 spindles/min, p=0.0177).

Figure 5A:
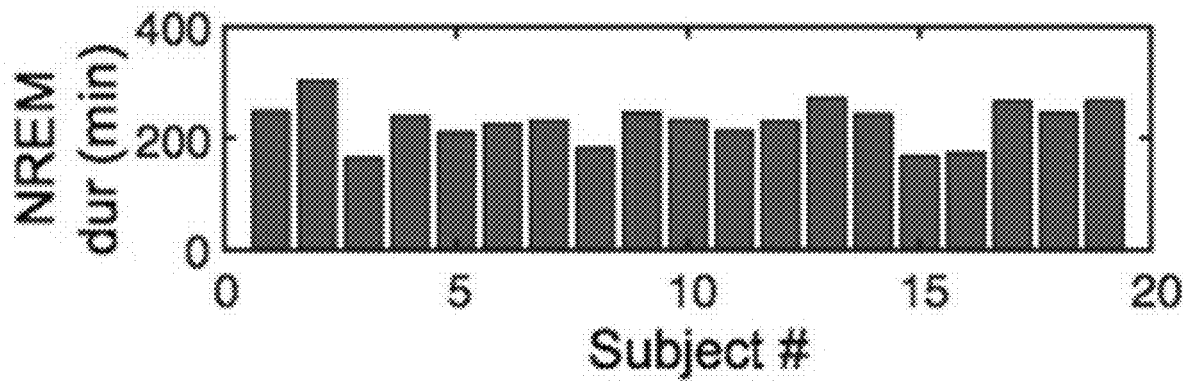
Figure 5B:
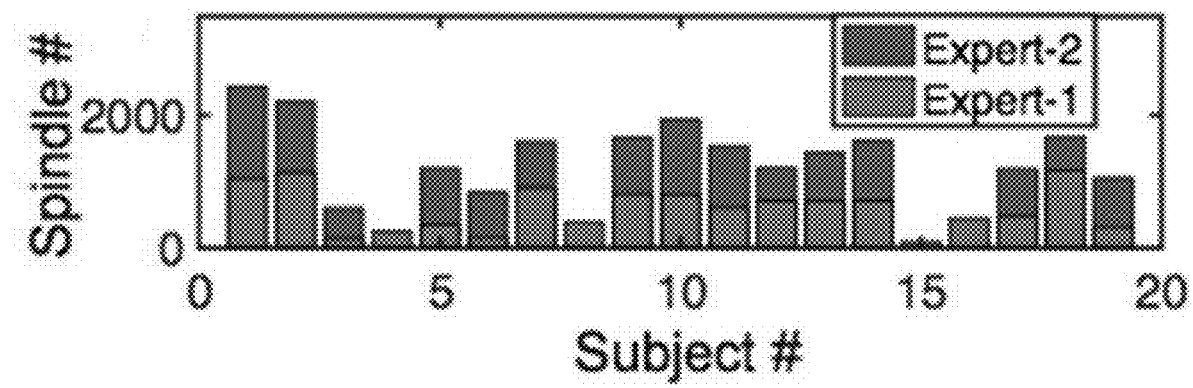
Figure 5C:
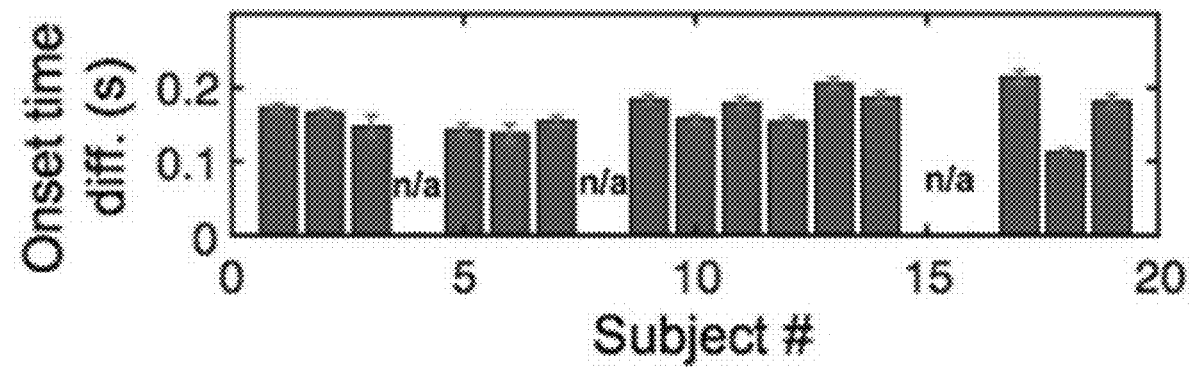
Figure 5D:
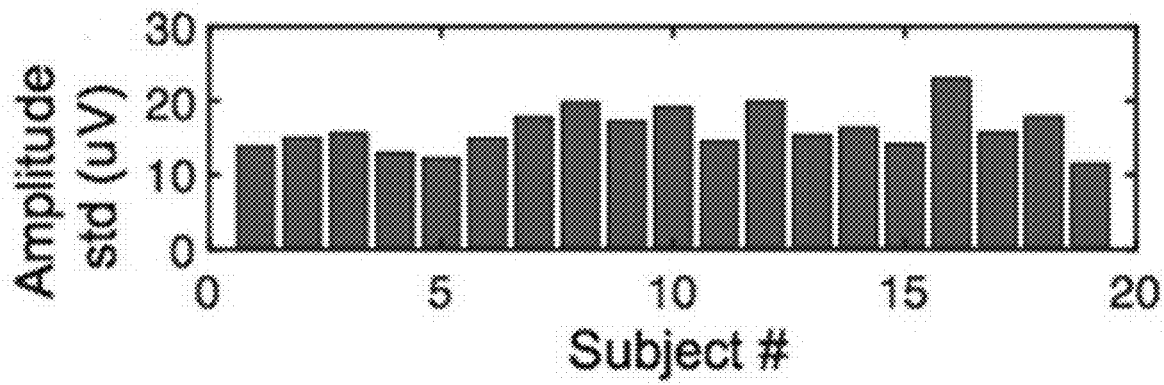
Figure 5E:
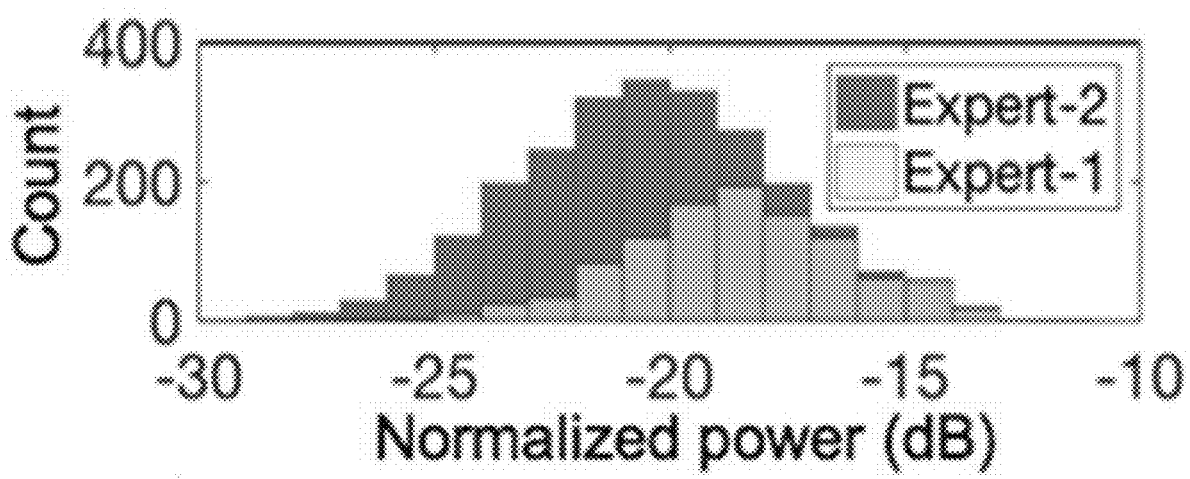
Figure 5F:
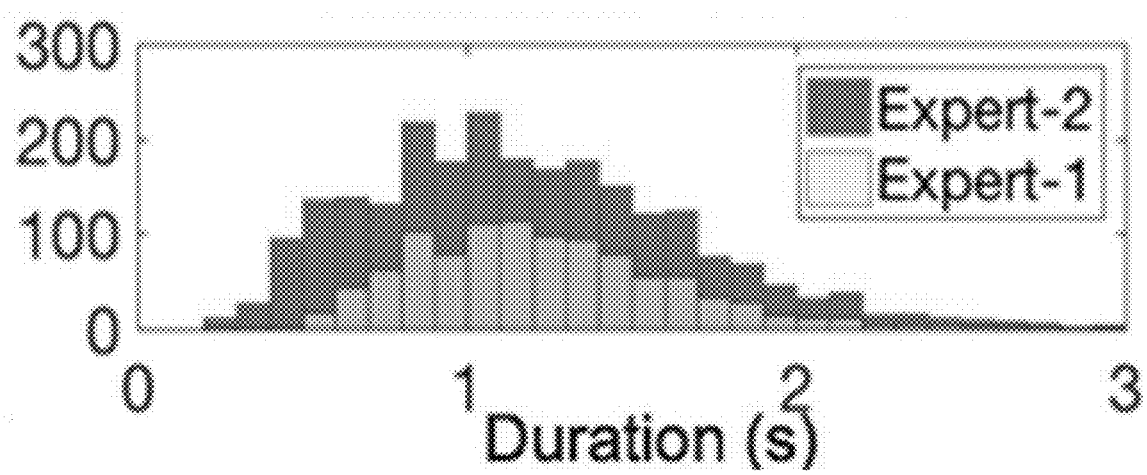
Figure 5G:
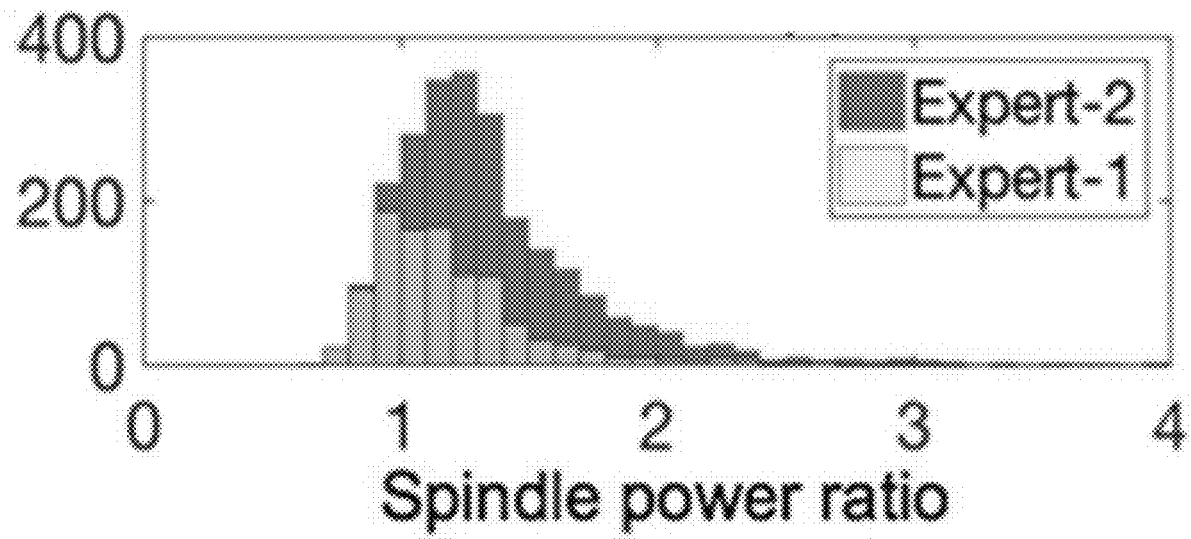
Figure 5H:
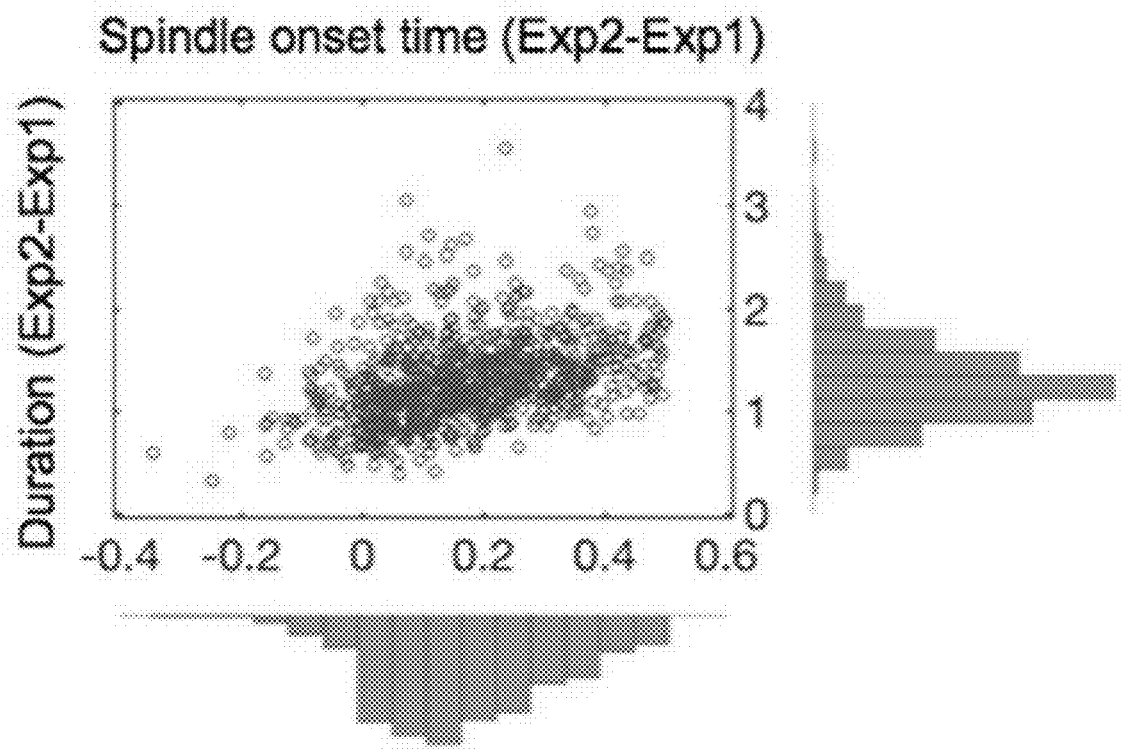

On the MASS dataset (n=19 subjects), SpindleNet achieved a mean detection latency of ~340 ms based on from the OR criteria (choosing the earliest onset) and ~205 ms based on the AND criterion (conservative onset, FIG. 8g)—these statistics are reasonable considering the uncertainty in expert labeling of spindle onset, FIG. 5c). In contrast, the McSleep algorithm is not suitable for online processing, thereby yielding no latency comparison. A detailed result summary is shown below in Table 1, which provides a summary of spindle detection performance of SpindleNet on MASS dataset (n=19 subjects).

TABLE 1

| MASS subject # | Cross validation fold # | Median latency (ms) | Sensitivity | Specificity | FDR | F1-score | AUROC | False event rate (spindles/min) | True event rate (spindles/min) |
|---|---|---|---|---|---|---|---|---|---|
| 1 | 1 | 250.85 | 0.8739 | 0.9888 | 0.0566 | 0.9072 | 0.9944 | 0.5517 | 9.1818 |
| 2 |   | 250.16 | 0.927 | 0.9829 | 0.1088 | 0.9087 | 0.9951 | 0.8892 | 7.2782 |
| 3 |   | 286.44 | 0.7142 | 0.9971 | 0.0572 | 0.8127 | 0.9954 | 0.1633 | 2.6917 |
| 4 |   | 215.09 | 0.9353 | 0.9633 | 0.2682 | 0.8211 | 0.99 | 3.5114 | 1.0182 |
| 5 | 2 | 269.76 | 0.7153 | 0.9919 | 0.1418 | 0.7802 | 0.9902 | 1.9859 | 5.4174 |
| 6 |   | 262.96 | 0.89 | 0.9672 | 0.1904 | 0.8479 | 0.9864 | 0.4571 | 2.765 |
| 7 |   | 355.86 | 0.7882 | 0.9926 | 0.0601 | 0.8574 | 0.9906 | 1.7033 | 7.2412 |
| 8 |   | 342.94 | 0.7355 | 0.9987 | 0.0096 | 0.8441 | 0.9953 | 6.3961 | 2.11 |
| 9 | 3 | 238.9 | 0.954 | 0.9597 | 0.2215 | 0.8574 | 0.9923 | 0.3857 | 6.0288 |
| 10 |   | 273.01 | 0.8854 | 0.9805 | 0.1681 | 0.8579 | 0.9912 | 0.0647 | 6.6039 |
| 11 |   | 227.11 | 0.9711 | 0.9414 | 0.3486 | 0.7798 | 0.9909 | 2.1067 | 7.4065 |
| 12 |   | 179.2 | 0.9774 | 0.9018 | 0.4145 | 0.7323 | 0.9807 | 1.0538 | 5.2166 |
| 13 | 4 | 333.87 | 0.9087 | 0.9829 | 0.1761 | 0.8642 | 0.9944 | 3.1616 | 5.9087 |
| 14 |   | 207.54 | 0.9444 | 0.9491 | 0.2721 | 0.8222 | 0.9888 | 5.1579 | 7.2868 |
| 15 |   | 223.6 | 0.9604 | 0.9609 | 0.3601 | 0.768 | 0.9927 | 2.4406 | 0.5715 |
| 16 |   | 47.91 | 0.9605 | 0.9404 | 0.7752 | 0.3643 | 0.976 | 4.0902 | 2.5528 |
| 17 | 5 | 58.425 | 0.9974 | 0.8895 | 0.7519 | 0.4977 | 0.9808 | 0.9449 | 4.4194 |
| 18 |   | 118.88 | 0.9897 | 0.9589 | 0.8102 | 0.3184 | 0.9938 | 2.6696 | 7.1434 |
| 19 |   | 114.9 | 0.9845 | 0.9288 | 0.6157 | 0.5528 | 0.9858 | 2.1905 | 3.8921 |

Notably, our false event rate was significantly lower (nearly half) compared to that derived from the McSleep algorithm. A representative FP example that was misidentified by the McSleep algorithm but correctly identified by our method is shown in FIG. 7a. We also obtained a higher Cohen's kappa value of 0.71±0.014 (McSleep: 0.45±0.035, p<0.0001), indicating a high degree of agreement between our detected spindle results and annotated ground truth (FIG. 7d). On DREAMS dataset, although SpindleNet performed better on some metrics, the performances of two methods were not significantly different (FIG. 7e,f), possibly due to a shorter sleep recording duration (30 min) or small sample size (n=6).

Figure 8C:
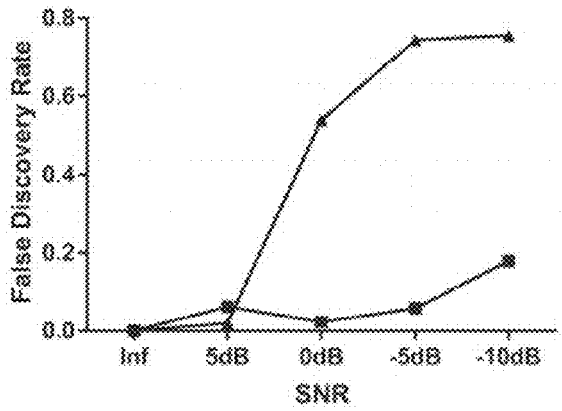
Figure 8D:
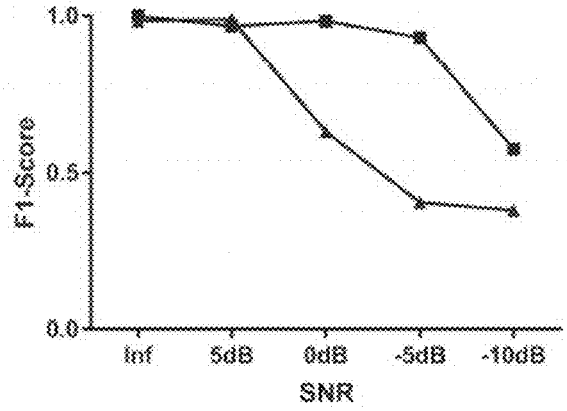
Figure 8E:
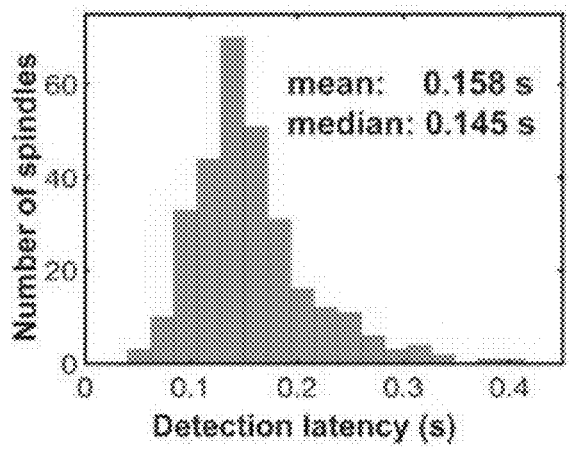
Figure 8F:
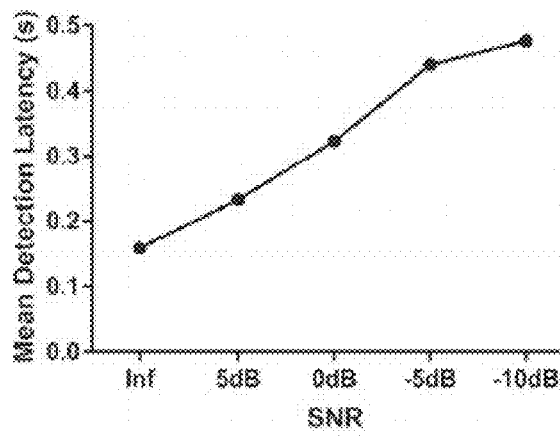
Figure 8G:
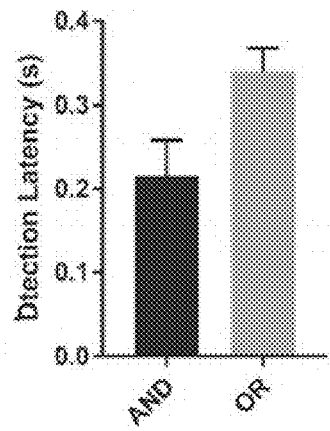

Next, we generated 30-minute EEG recordings containing synthetic spindles (density: 10 spindles per minute) with varying spindle durations (0.3-1.2 s). Unlike human-labeled spindles that contain expert variability, the ground truth of synthetic spindles (onset and duration) is predetermined. We varied the SNR of EEG signals during testing and compared the detection performance of our method and the McSleep algorithm. At the level of infinity (noiseless) or 5 dB SNR, the performances of these two methods were similar. However, when the SNR was reduced to 0 dB or below, SpindleNet showed superior performance in all detection performance categories (i.e., sensitivity, specificity, FDR and F1-score; FIG. 8a-d). In the noiseless condition, SpindleNet achieved a mean detection latency of 150 ms during online spindle detection (FIG. 8e), and the mean detection latency degraded gradually with a decreasing SNR (FIG. 8f). When the detection latency is not a concern, the off-line detection performance could be slightly improved in comparison with on-line detection (FIG. 15).

Transfer Learning

Sleep spindle characteristics (e.g., power, duration, and frequency) are known to vary with age, health condition, and species. However, it is costly to annotate large amount of sleep spindles from EEG recordings from all groups. Therefore we explored transfer learning to understand how knowledge learned from one domain (such as sleep spindles in healthy young adults) can be transferred to other domains.

Figure 16A:
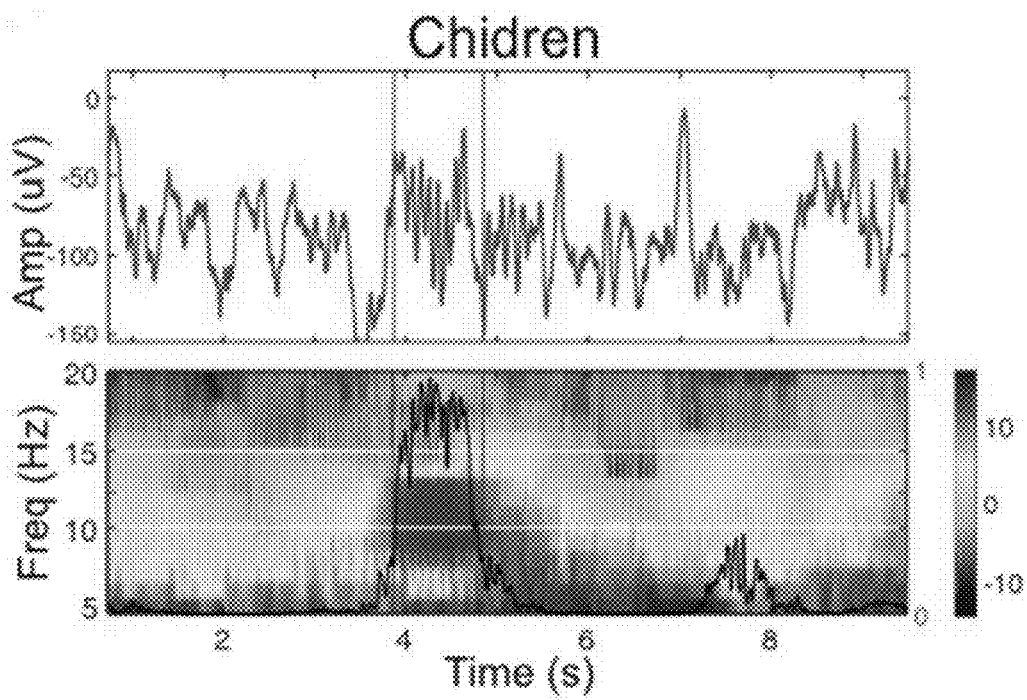
Figure 16B:
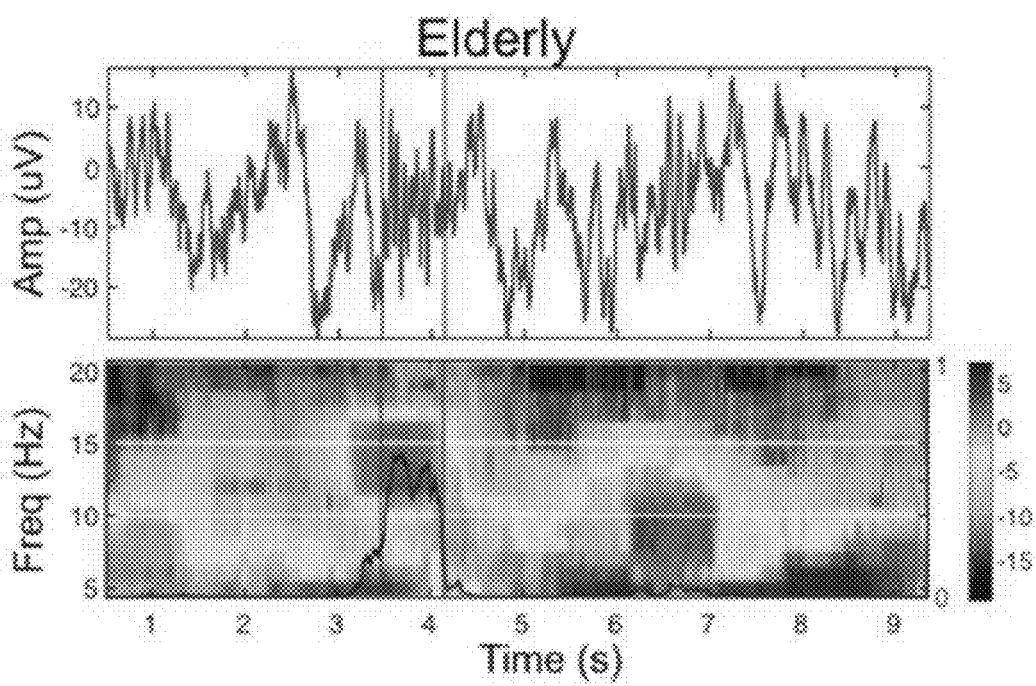
Figure 16C:
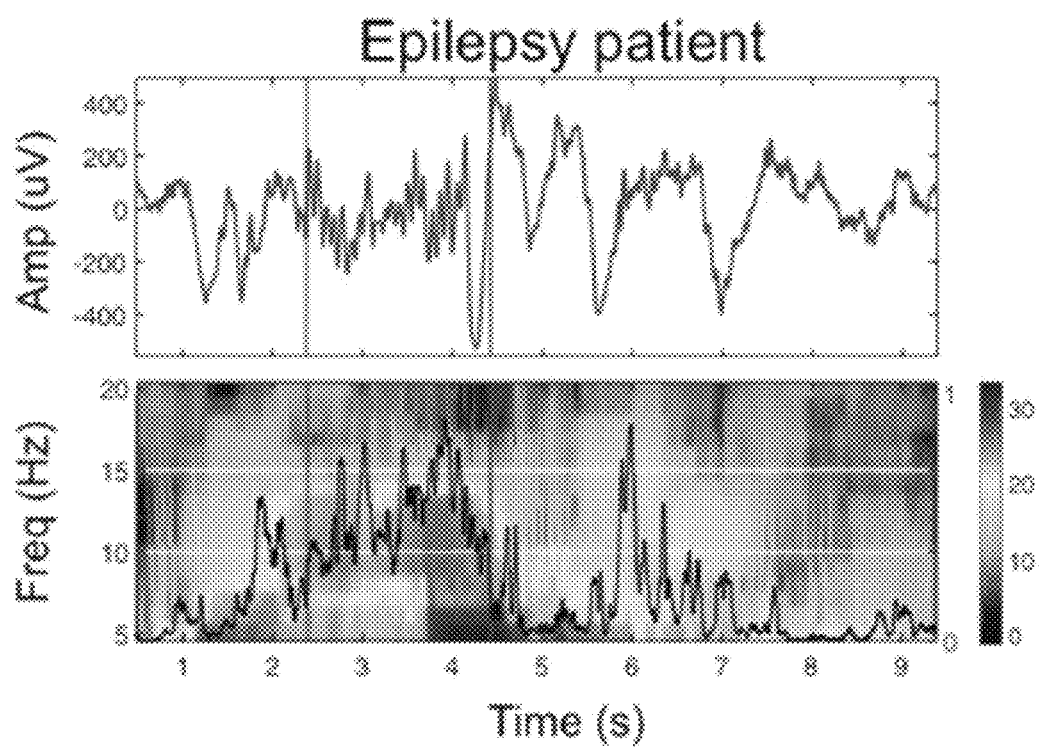
Figure 16D:
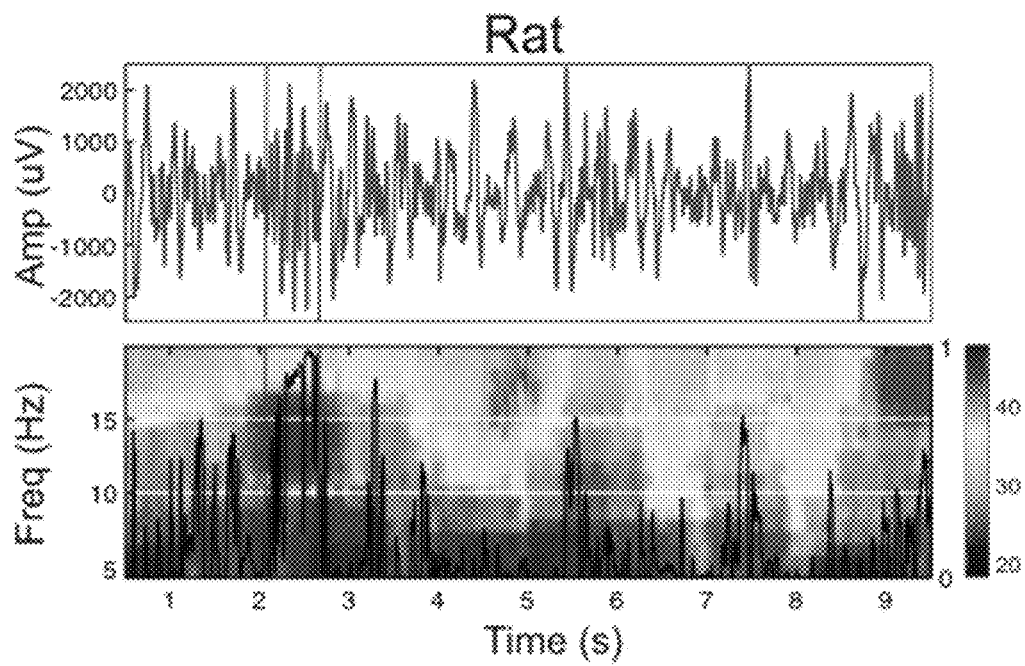
Figure 16E:
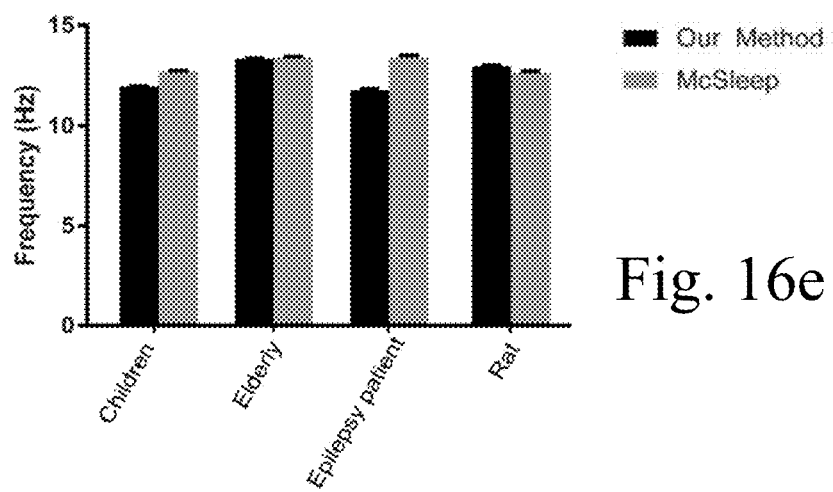
Figure 16F:
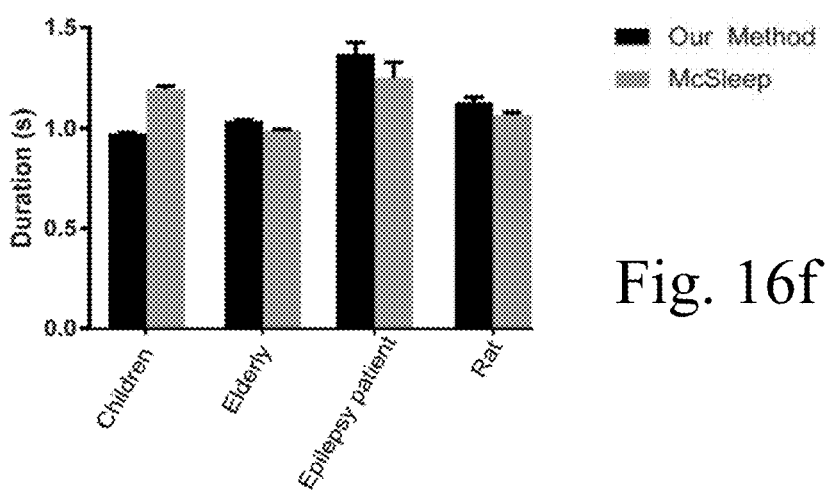
Figure 16G:
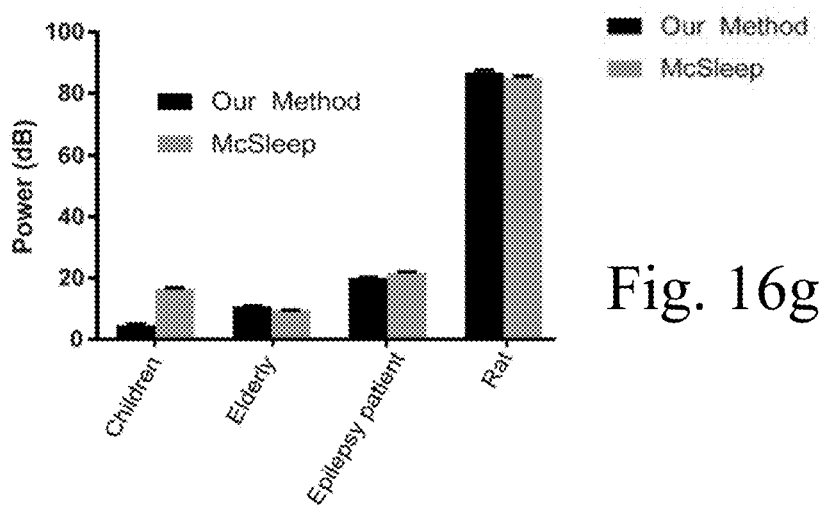

Between different sleep recordings, the amplitude/duration/frequency statistics of EEG or spindle features might vary significantly. We first tested SpindleNet on un-annotated human EEG sleep recordings from three distinct age groups, first from young children (n=5, ages 5-9.9 years), second from elderly subjects (n=6, ages 65-89 years), and third from epilepsy patients (n=3, ages 17-26 years). FIG. 16a-c shows representative examples our spindle detections in these sleep datasets. Next, we investigated whether the knowledge of human sleep spindles can be transferred to animal sleep research, a significantly more challenging task. Due to the lack of annotated sleep spindles in rats, it is difficult to directly train a DNN based on rat local field potential (LFP) recordings. To remove slow oscillations and potential low-frequency artifacts, we applied band-pass (2-50 Hz) filtering to LFP signals before feeding them to SpindleNet. Rats have a different distribution than humans of sleep EEG power at various frequency bands, so we did not use power features for rat sleep spindle prediction. Although we only used the temporal features, SpindleNet was still able to identify spindles in rat LFP recordings (FIG. 16d). Due to the lack of ground truth, we could not quantify the TP and FP rates. Instead, we compared the spindle characteristics derived from SpindleNet with those from the McSleep algorithm (FIG. 16e-f). Results show that SpindleNet generated spindle statistics comparable with the McSleep algorithm.

Discussion

We have proposed a deep learning approach (SpindleNet) for real-time sleep spindle detection. In the context of learning single-channel EEG patterns, the CNN is aimed at extracting or detecting scale-invariant oscillatory features of EEG signal (such as spindle oscillations), whereas the RNN is aimed at modeling the temporal structure of those features. In contrast to imaging processing, CNNs or CNN+RNN architectures are been used sparingly in EEG processing. By constructing a large number of labeled samples (from either annotated EEG traces or synthetic examples), our DNN approach is capable of detecting spindles with high accuracy (FIG. 6e,f) and short detection latency (FIG. 8e), as confirmed by multiple independent spindle datasets and synthetic spindle simulations. We further validated that the learned knowledge of SpindleNet from human sleep can be directly transferred to identify rat sleep spindles, despite the between-species difference in spindle statistics. This will impact animal sleep research, as it is time-consuming to annotate sleep recordings under irregular sleep conditions during the course of murine experiments, and there is lack of labeled data given relatively shorter sleep recordings. SpindleNet is also insensitive to the sampling frequency of EEG recordings (FIG. 6g) and robust to noise (FIG. 8a-g). This suggests that it might be directly applied to wireless EEG-based sleep recordings with low sampling rate transmission for preservation of bandwidth or battery power.

SpindleNet has several key benefits over other spindle detection methods. Most spindle detection methods rely on offline processing of filtered EEG data followed by various thresholding schemes. The online spindle detection method proposed in [Lustenberger et al., 2016, *Current Biology*] employed an open-source system (rtxi.org) and adaptive threshold-based detection method; but no detection latency was reported. However, threshold-based detection methods are often sensitive to selection of globally optimal thresholds, and the threshold adaptation is purely heuristic. SpindleNet bypasses these limitations by learning the higher-order spectrotemporal filters and temporal structures. In addition, previous methods have limited scalability across subjects, diseases, and species since they require hand-tuned features and parameters. In contrast, our method is able to generalize across datasets and learn the common spectrotemporal features. Finally, since SpindleNet is able to learn spindle characteristics that are most discriminative for spindle detection, it performs consistently better on multiple performance metrics compared to other detection methods (FIG. 7a-g).

SpindleNet is capable of extracting complex features from large amounts of time-series data, and is also conceptually different from previous applications of DNN in EEG data classification. While the previous research has primarily relied on applying CNNs or RNNs to EEG data in a single domain, here we process the EEG data in the time-domain using a combination of CNN and RNN, in addition to power features.

Real-time detection of sleep spindles has potential applications in closed-loop neuroscience experiments, where the onset of sleep spindle can be used as a neurofeedback of BMIs to trigger an optogenetic intervention, auditory stimulation, or transcranial current stimulation. For instance, the theory of TMR is built upon the assumption that pairing memory cues with brain oscillations at certain phase may mediate effective memory consolidation. Therefore, ultra-fast detection with the shortest detection latency would be desirable, as the strength or effectiveness of memory enhancement depends on the timing of acoustic or electrical stimulation. SpindleNet can be extended to multi-channel EEG recordings for identifying patterns of propagating spindle waves. Same analysis is also applicable to MEG or ECoG recordings, which might have higher sensitivity for spindle detection. In addition, SpindleNet is suitable for sleep monitoring, since an accurate characterization of dysfunctional spindle activity, in combination with other metrics, can help diagnose a thalamic dysfunction or neurodevelopmental disorders.

Since spindles and SOs are temporally coupled during NREM sleep (FIG. 6d), it may be important to simultaneously detect spindles and slow wave activity. It has been reported that fast (13-16 Hz) spindles are coordinated with depolarizing cortical up state, whereas slow (9-12 Hz) spindles are commonly coordinated with hyperpolarizing down state, implying that slow and fast spindles may represent different classes of sleep events with possibly distinct sources of generation. In the examples described herein we have limited our analysis to single-channel spindle detection, and have not investigated spatial spindle statistics. However, it is contemplated that further identification of the subcategory of sleep spindles and their spatiotemporal patterns may reveal additional information in healthy or diseased brains.

We have compared SpindleNet with the McSleep algorithm for automatic spindle detection. As these two methods are used rather differently (in terms of training, sample size requirement, channel requirement, online vs. offline), a fair comparison might not be completely possible. Nevertheless, the robust detection performance derived from SpindleNet highlights the strength of data-driven deep learning. However, a comprehensive comparison between different sleep spindle methods would require a completely independent and unused large annotated spindle dataset. Our proposed transfer-learning paradigm can be further extended along two research lines: first, use of generalized adversarial network to generate synthetic rodent sleep spindles for training; and second, integration of human and rodent sleep spindles during neural network training. In general, simultaneous use of multiple sources of information or domain knowledge may boost detection performance in transfer learning.

Finally, it is also contemplated that our deep learning approach may be generalized to detect other EEG oscillations during distinct neural states. This is particularly interesting for EEG oscillations with similar frequency content as sleep spindles, such as the alpha and mu rhythms. Alpha waves are EEG oscillations in the frequency range 9-15 Hz, and occur during relaxed mental state. Detection of pre-stimulus alpha waves may be useful in predicting mistake or lapse-of-attention. The alpha oscillatory activity may also emerge during the so-called "alpha-delta sleep", an abnormal intrusion of alpha activity into the delta wave during NREM sleep. The mu rhythm can be found in the sensorimotor cortex and is affected by voluntary movement or the intention to move. Human EEG mu-rhythms have been widely adopted in the motor imagery BMI, as well as the assessment of child development (e.g., infant's ability to imitate) and autism.

Methods

Experimental Data.

We tested our deep learning approach on four publicly available human sleep datasets, one non-public human sleep spindle data set, and one non-public rat sleep dataset. All studies were approved by the New York University School of Medicine (NYUSOM) Institutional Review Board (IRB) and Institutional Animal Care and Use Committee (IACUC).

The first human sleep spindle dataset was derived from the Montreal archive of sleep studies (MASS)—an open-access and collaborative database of laboratory-based polysomnography (PSG) recordings. MASS is composed of several cohorts divided into subsets. Cohort one has five subsets and comprises of 200 complete night PSG recordings of 97 men and 103 women of age varying between 18 and 76 years (mean±SD: 38.3±18.9 years), stored in European data format (EDF). The subset #2 within cohort one (19 healthy subjects) was annotated for N2 stage spindles (start-time and duration) by two human experts based on the C3 channel (linked-ear reference). A total of fifteen subjects were annotated by two human experts, whereas the remaining four subjects were annotated by only one expert. The EEG signals were originally sampled at 256 Hz and resampled to 200 Hz for standardization. For each subject's sleep recording, we observed consistent variability between the annotations of the two experts in terms of start-time, duration and total number of spindles (FIG. 5a-h). In our study, we used the union of annotations from the two experts as our ground-truth in training the neural network. We also evaluated the performance using an intersection of the annotations from the two experts, which resulted in lower performance. We used the MASS dataset for the 5-fold cross-validation analysis, and tested the performance of the algorithm on the other independently acquired datasets.

The second human sleep spindle dataset was derived from the DREAMS database from the University of MONS-TCTS Laboratory and Universite Libre de Bruxelles—CHU de Charleroi Sleep Laboratory under terms of the Attribution-NonCommerical-NoDerivs 3.0 Unported (CC BY-NC-ND 3.0) License. The DREAMS dataset consists of 30 minute PSG excerpts from eight subjects (4 males and 4 females, age: 45.88±7.87 years) with various sleep pathologies (dysomnia, restless syndrome, insomnia and apnea/hypopnea syndrome. The excerpts contain three EEG channels (FP1-A1, C3-A1, O1-A1), two EOG channels and one EMG channel. They were scored independently by two sleep experts based on the C3 channel. The original EEG recordings had varying sampling frequency of 50-200 Hz, and then were uniformly resampled to 200 Hz for standardization. Since not all EEG recordings were annotated by two experts (six only by one expert), and there were consistent differences in their annotations (for e.g. expert two only annotated the start-time while expert one annotated both start-time and duration of the spindles), we used the union of their annotations ('OR' criterion) as the ground-truth to assess the performance of the sleep spindle detection.

The third and fourth human sleep datasets were derived from the national sleep research resource (NSRR) repository. The third dataset consisted of overnight PSG recordings from elderly men (65 years or older), collected as a part of a multi-center study of osteoporotic fractures (MrOS). The fourth dataset consisted of overnight PSG date from children (ages 5 to 9.9 years) collected as a part of a multi-center childhood adenotonsillectomy (CHAT) study. Both datasets consisted of EEG recordings for channels C3 and C4 with expert-annotated sleep-stages. Original sampling rates varied from 200 Hz to 512 Hz, and were uniformly resampled to 200 Hz. We randomly selected five subjects from each dataset and tested SpindleNet on stage-2 NREM sleep data from channel C3.

The fifth human sleep spindle dataset consisted of intracranial EEG (iEEG) recordings (on average 120 electrodes per subject) from a study of 18 epileptic patients who underwent surgery for invasive monitoring. The original signal was sampled at 512 Hz and resampled to 200 Hz. We selected three subjects who had entrained sleep spindles following randomly applied acoustic stimuli.

Finally, for rat sleep recordings, multichannel LFP signals were acquired from the rat primary somatosensory region across four sessions (1-2 hours duration) from three animals (male Sprague-Dawley rats). Rats were kept with controlled humidity, temperature, and 12 hour (6:30 AM to 6:30 PM) light-dark cycle. Food and water were available ad libitum. Rats were anesthetized with isoflurane (1.5-2%) and implanted with silicon probes (NeuroNexus) mounted on custom-built microdrives. One or two probes were implanted in the right hemisphere. The coordinates for S1 implantation were: AP −1.5 mm, ML+3.0, and DV −1.5. Rats were allowed to recover for about one week after surgery. Rats were allowed to habituate in the recording room and remained in their home cage with food and water available during the daytime for 5-7 days. Lights were on in the recording room during the recording. Raw neural signals were recorded with 64-ch digital headstage (RHD2132, Intan Technologies) and acquisition board (Open Ephys) at a sample rate of 1 kHz (resampled to 200 Hz for standardization). To obtain LFPs, we further filtered the signal by a bandpass filter between 0.3 and 300 Hz.

Training Setup for SpindleNet.

We used exponential linear units (ELUs) as the activation function for all the CNN units due to its demonstrated faster learning time and higher accuracy compared to other types of nonlinearity. Every layer was followed by max-pooling using a filter size of five samples and stride equal to one. The CNN with ELUs has been previously tested in EEG data analyses. The dropout strategy has been shown to outperform other regularization methods, which randomly sets a specified percentage of input units in every layer (except the first layer) to zero. In all experiments, we empirically set the dropout rate equal to 0.5.

The temporal input for online spindle prediction consisted of single-channel EEG (or LFP) signal with a moving window of length 250 ms, approximately one quarter of the average spindle size. The parameters of SpindleNet were updated using the Adam optimizer. We used the following default learning hyperparameters: an initial learning rate of 0.0001 and mini-batch size of 500 (with a balanced size of examples from two classes).

We used 70% of all balanced augmented samples as the training set, 20% for validation and 10% for testing. We tested SpindleNet on the complete dataset by using a moving window with a stride of one. For each training sample, we preprocessed the sample by detrending, demeaning, and scale normalization for calibration.

Data Calibration.

In practice, EEG signals have different amplitude or variance statistics depending on the sleep stage, electrode conductance, and recording depth. Therefore, we applied scale normalization for data calibration. For the current experimental testing, the scale was chosen as the average standard deviation of the expert-annotated spindles). Notably, the spindle detection accuracy was robust to the calibration scale (FIG. 17).

Data Augmentation.

The occurrence of spindles was distributed throughout stage-2 or stage-3 NREM (N2, N3) sleep with a density that varied by subject and pathology. This resulted in an imbalanced dataset with few samples from the positive class (spindle) compared to the negative class (non-spindle baseline). To generate a balanced training sample size, we augmented the positive and negative class until they were balanced. This was done by selecting a fixed time interval before and after the center of the spindle and generating samples using a moving window of size $T_W$ with a stride of one. A positive label was generated for every window of length $T_W$ if more than 50% samples within that window overlapped with the expert-annotated spindles; otherwise a negative label was used (FIG. 10).

Feature Selection and Fusion.

Spindles are characterized by a localized high power in the spindle band (9-16 Hz) of spectrogram. To accommodate additional spectral features, we computed the multi-taper spectrum using a time window of 500 ms and step size of 5 ms (i.e., 1/sampling frequency). The power features were computed after data preprocessing. In addition, we computed the spectral power ratio $$\frac{\text{spindle}(9-16\text{ Hz})\text{band}}{\text{delta} + \text{theta}(2-8\text{ Hz})\text{bands}}$$

as one of the features. The power features were appended to the output of the RNN in two subnetworks (FIG. 4a).

Online Vs. Offline Detection of Sleep Spindles.

Depending on specific application, we employed different criteria to define sleep spindles. In online spindle detection, the latency is the most important factor. Detection latency is not an issue for offline spindle detection applications, therefore we used a stricter duration criterion to eliminate the detected events shorter than a specified length (e.g., 400 ms).

Assessment of Performance.

We used the following performance metrics:

$$\text{Sensitivity} = \frac{TP}{TP+FN}, \text{Specificity} = \frac{TN}{TN+FP},$$

$$\text{Precision} = \frac{TP}{TP+F}, \text{Accuracy} = \frac{TP+T}{TP+FP+TN+F},$$

$$F1\text{-score} = \frac{2 \times TP}{2 \times TP+FP+FN},$$

$$\text{False positive rate}(FPR) = \frac{FP}{FP+TN}, \text{ and}$$

$$\text{False discovery rate}(FDR) = \frac{FP}{FP+TP},$$

where TP (true positive) denotes agreement between the algorithm and ground truth. FN (false negative) denotes a true spindle was missed by the algorithm but marked by experts. FP (false positive) denotes a spindle was detected by algorithm but not marked by the experts. TN (true negative) was defined as: TN=signal duration in seconds-FP-TP-FN. We assess a true positive when the absolute difference between the estimated spindle onset by the algorithm and the onset of ground truth is less than 0.25 s.

We also computed the false event rate and true event rate (per minute). Specifically, we used a non-overlapping 1-min moving window to calculate the statistics of spindle events (regardless of the duration). In addition, we computed the detection latency by comparing the spindle onset detected by SpindleNet to that of the experts' annotation.

Synthetic Spindle Generation.

We used a quadratic parameter sinusoid (QPS) model to characterize sleep spindles:

$$s(t) = e^{(a+bt+ct^2)} \cos(d+et+ft^2)$$

where a, b, c, d, e and f are the free parameters of the quadratic functions. We set a=0 (such that the peak amplitude is 1, or $s_{max}(t)=1$) and set b, c, d, e, f as random variables with normal distributions derived from the annotated spindle statistics. To mimic the rich spectrotemporal components of raw EEG data, we merged the synthetic spindles with experimental EEG signals. The peak of a simulated spindle was centered at 0. To define the onset/offset of simulated spindle, we defined the threshold to be at 0.4 (i.e., 40% of the peak amplitude of s(t). (FIG. 14). We used a Butterworth 'bandstop' filter to obtain a clean baseline EEG by removing 9-16 Hz frequency components. Adding these two components together with (optional) broadband noise yielded synthetic spindles (FIG. 14).

Other Sleep Spindle Detection Methods.

There are numerous automatic sleep spindle algorithms in the literature, but the majority of them are not suitable for online applications. In addition, some algorithms require prior knowledge or parameter fitting, therefore it is nearly impossible to have a completely fair comparison between methods.

For the purpose of comparison, here we selected a recently published spindle detection algorithm known as McSleep (https://github.com/aparek/mcsleep.git), which has been shown to outperform seven other spindle detection methods in the MASS and DREAMS datasets. The McSleep algorithm is a nonlinear subspace detection method, which decomposes the input EEG signal into the sum of a transient and an oscillatory component. The envelope of oscillatory activity is further detected by a Teager operator, followed by spindle threshold detection.

Assessment of Agreement Between Detection Results.

Cohen's kappa and other kappa variants are commonly used for assessing inter-rater reliability (IRR) for nominal (i.e., categorical) variables. Kappa statistics measure the observed level of agreement between two raters or classifiers for a set of nominal ratings and corrects for agreement that would be expected by chance. Specifically, we computed kappa based on the equation $$\kappa = \frac{P(a) - P(e)}{1 - P(e)}$$

where P(a) denotes the observed percentage of agreement, and P(e) denotes the probability of expected agreement at a chance level (for a two-class classification problem, P(e)=0.5). κ=1 denotes a perfect agreement.

Example II

Poor quality sleep has been shown to be a risk factor for chronic pain, with numerous studies implicating sleep in pain-associated depression and anxiety as well. A causal link between chronic pain and sleep deficits, however, is not well established. Nevertheless, there are reports that suggest interventions during sleep may have potential benefits in treating pain. Thus, objective measurements of sleep quality present a promising diagnostic and therapeutic target for pain.

In Example II, we show that in a chronic inflammatory pain model in rodents, there is a significant decrease in sleep spindle activity compared to controls. This suggests that sleep spindles may serve a role in the development of much-needed noninvasive and objective biomarkers for pain states. Methods to restore sleep spindles, meanwhile, is associated with decreased pain symptoms. These results suggest that sleep spindle density correlates highly with chronic pain and may thus be both a potential biomarker for chronic pain and a target for neuromodulation therapy.

Results

Figure 18:
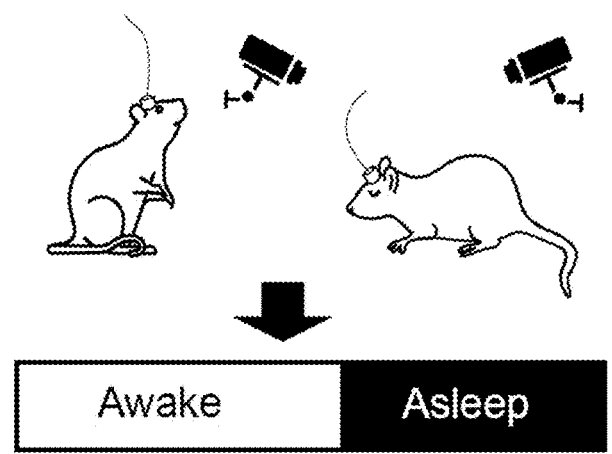
FIGS. 18 through 23 show experimental data obtained according to Example II described in the present application.
Figure 19A:
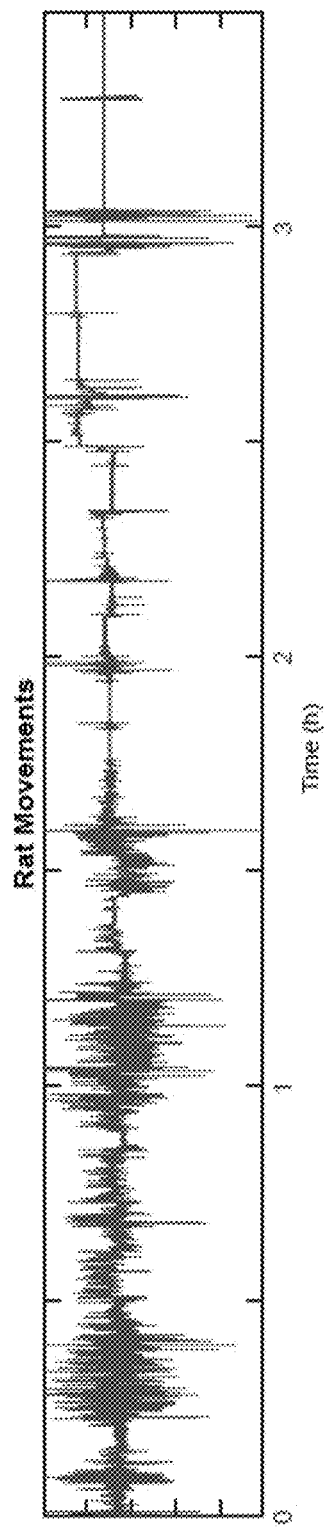
Figure 19B:
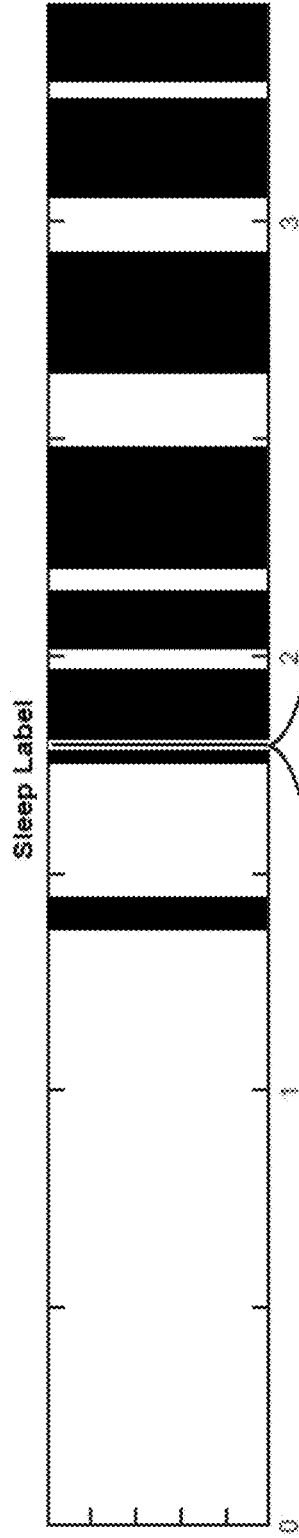
Figure 19B:
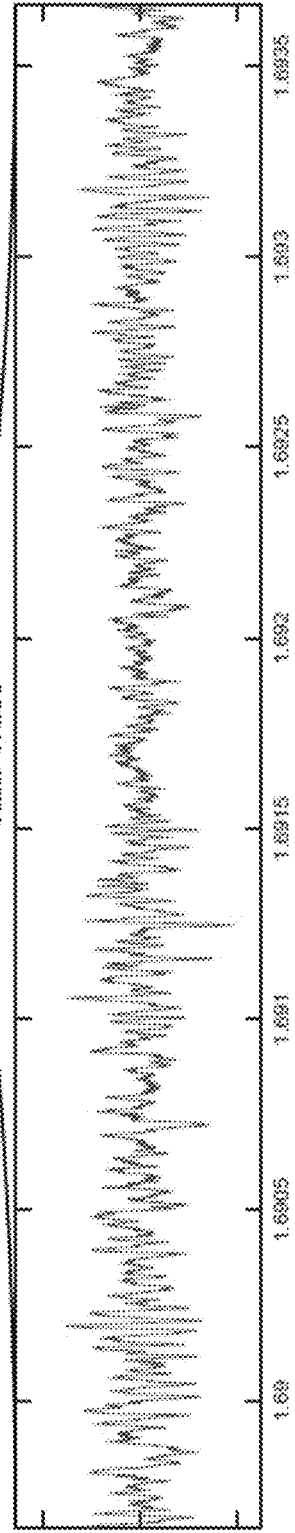

Each rat slept for a minimum of 1 hour in the sleep recording apparatus for every 3 hours of experimentation (FIG. 18). Sleep vs. wake state was classified based on the video and accelerometer measurement of rat's movement (FIGS. 19a, b), and such classification was used to search for sleep spindles given the EEG signal (FIG. 19b). Overall, sleep duration did not differ significantly between experimental groups, recording days, or experiment sessions.

Figure 20A:
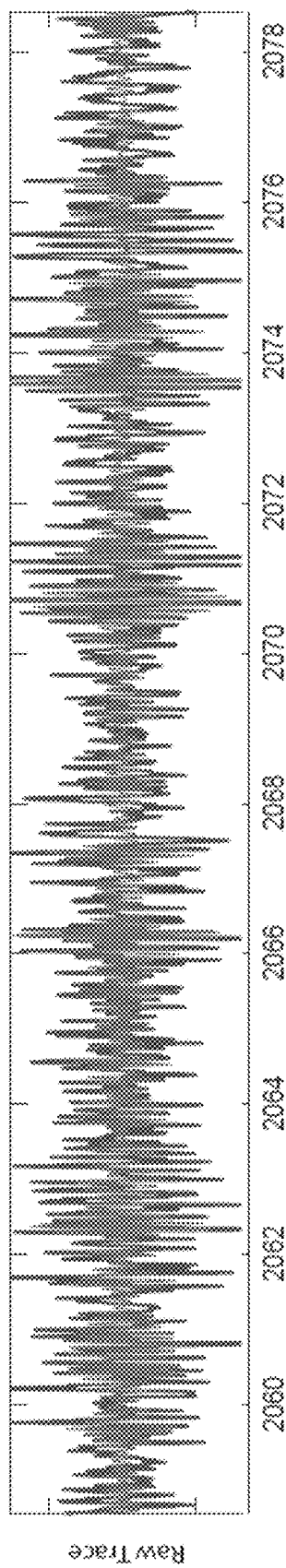
Figure 20B:
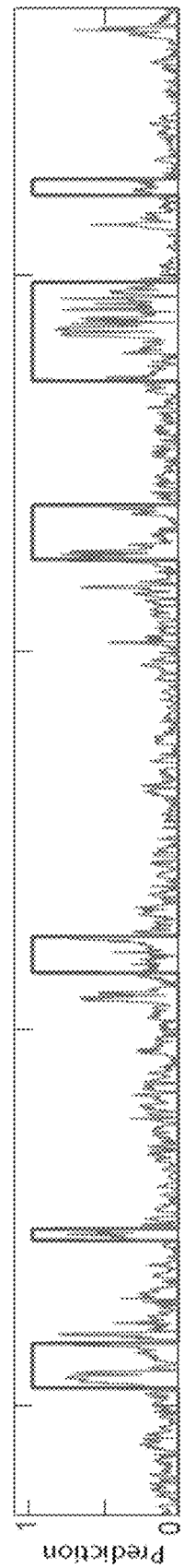
Figure 20C:
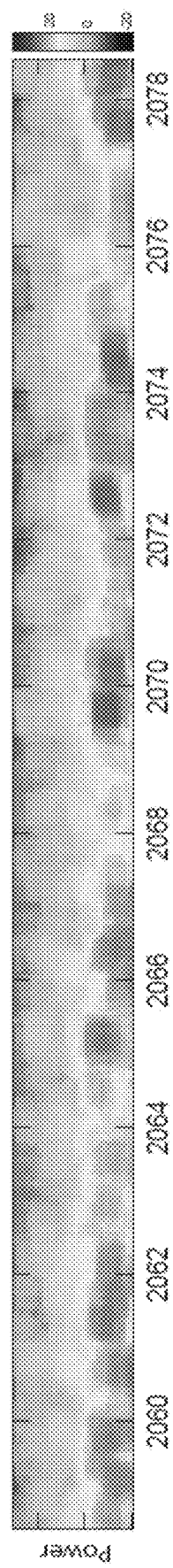

A deep neural network, SpindleNet, as described above in Example 1, automatically detects spindle episodes in real time (FIGS. 20a-c). The output of SpindleNet provided soft thresholds for the detection of spindles (FIG. 20b), which were left consistent across all rats and sessions to allow correlations across time. SpindleNet rejected any spindles that did not meet the minimum duration criterion (1 s for rats) necessary to be considered a spindle episode. Detected spindles that met our pre-determined probability threshold and the minimum duration criterion were counted for the duration of the sleep session. We computed the relative spindle density measures by the ratio of the number of isolated spindles (detected by SpindleNet) per minute of sleep (exclusively for NREM sleep). Our SpindleNet can be easily integrated with any neuromodulation method in open- or closed-loop stimulation.

Figure 21A:
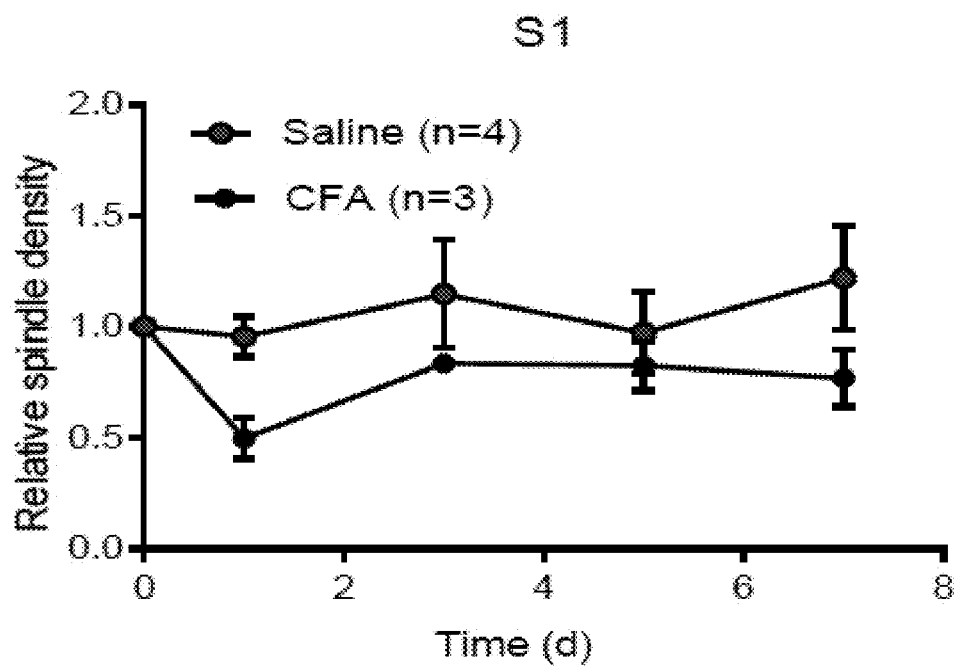
Figure 21B:
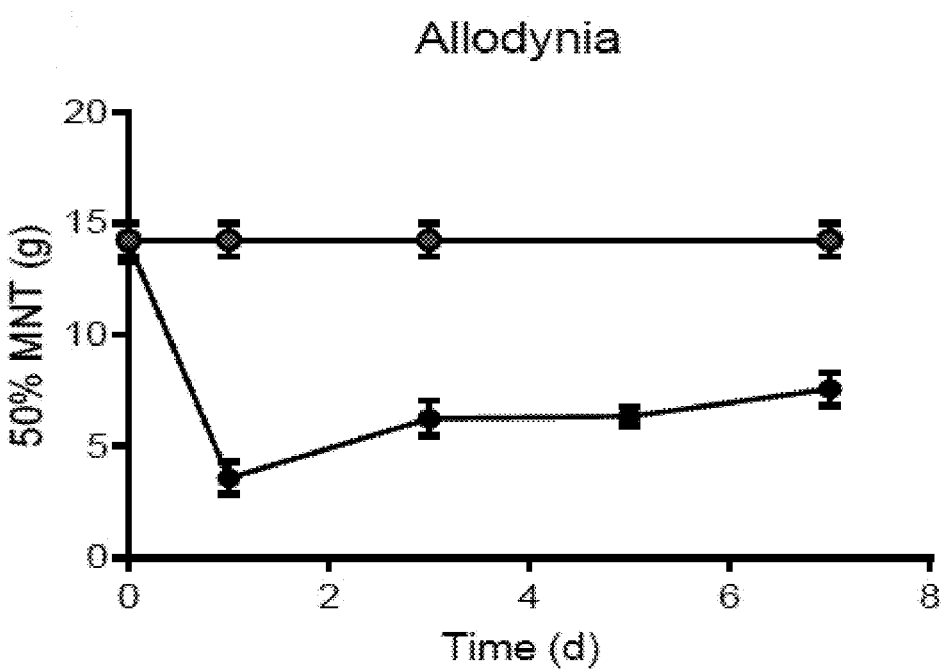
Figure 21C:
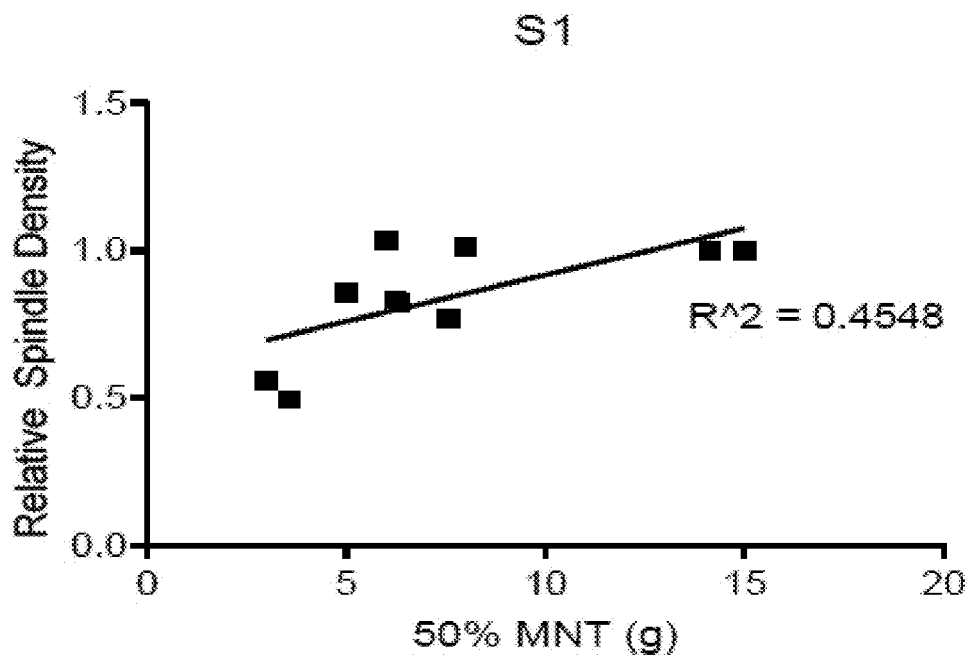

Our first research question is to investigate the impact of chronic pain on sleep spindles. We used Complete Freund's Adjuvant (CFA) to induce persistent inflammatory pain in the hind paws. We found that CFA-treated rats, compared with saline-treated rats (controls), showed a marked reduction in spindle density during sleep one day after the onset of pain. We correlated these relative spindle densities with behavior by measuring the mechanical nociceptive threshold, and we found that rats with increased allodynia have reduced spindle activity during sleep (FIG. 21a-c). As rats recovered from CFA, spindle density returned to baseline or the pre-CFA levels.

In contrast, control rats showed no symptoms of mechanical allodynia, nor did they show changes in spindle density over the time course of the experiment. We observed an inverse correlation between relative spindle activity and allodynia (FIG. 21c), indicating a close relationship between sleep spindle density and persistent pain. These results also suggest that spindle density may be a biomarker for the severity of pain.

Figure 22A:
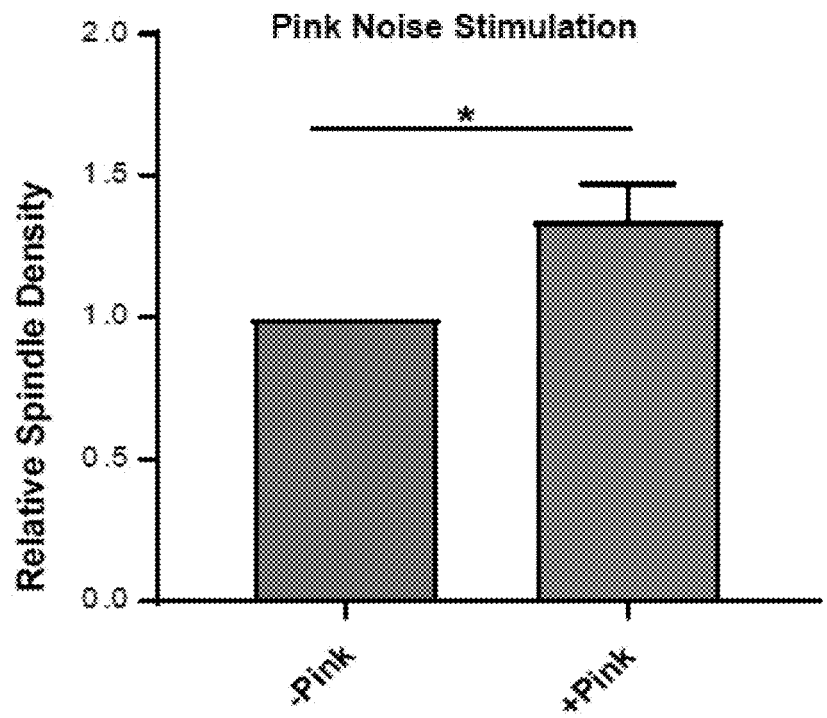
Figure 22B:
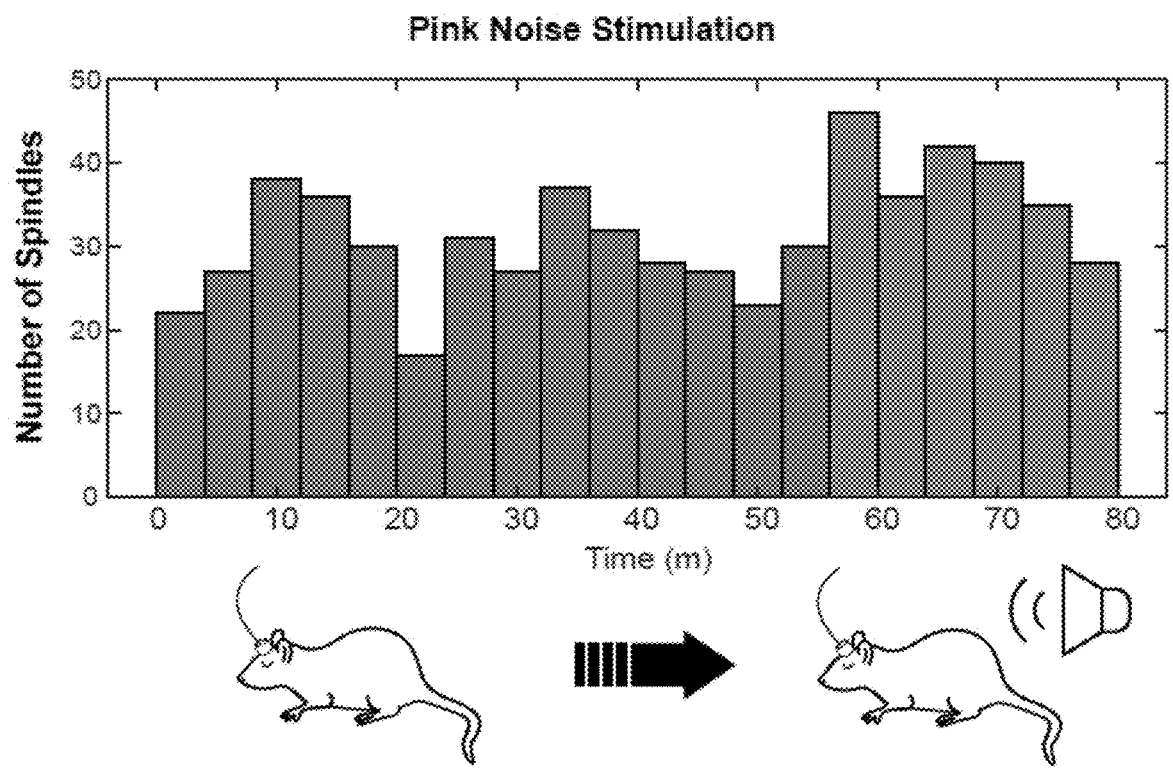
Figure 23:
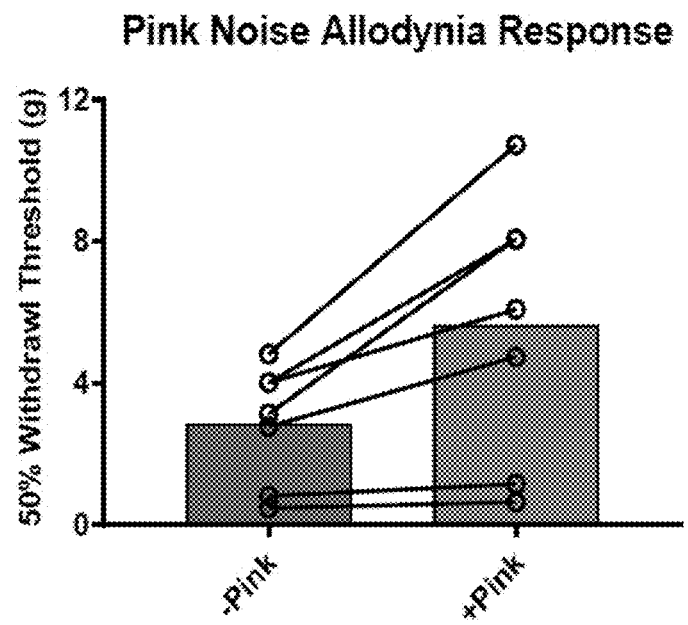

In Example II, we also investigated whether acoustic stimulation can affect sleep spindles and chronic pain symptoms. To dissect a possible causal relationship between pain symptoms and sleep deficits, we analyzed if restoration of sleep spindles could relieve pain. Pink noise, a type of low frequency acoustic stimulation, is a method for enhancing sleep spindles. In particular, pink noise is a signal having a frequency spectrum such that the power spectral density is inversely proportional to the frequency of the signal. Thus, we introduced random pink noise based on a Gaussian random distribution with average interval between stimuli of 10 seconds. Rats subject to such noise showed an immediate intra-session increase in spindle density (FIG. 22a-d). Detected sleep spindles had an average frequency between 10-15 Hz with variable duration (FIG. 22d). There was no statistically significant difference in the shape of spindles in the context of pink noise and spindles in the absence of pink noise, with both sets of spindles exhibiting the same frequency, duration, and power distributions. We further examined the effect of pink noise on pain symptoms. In order to maximize the treatment effects of acoustic stimulation, we exposed rats to 14 consecutive days of acoustic stimulation. We used spared nerve injury (SNI) to model stable chronic pain. SM-treated rats were exposed to 14 consecutive days of pink noise stimulation during 8 hours of sleep in a quiet room. We measured allodynia response before and after the pink noise treatment regimen, and observed a statistically significant change in behavioral pain response as manifested by relief of mechanical allodynia (FIG. 23). Together, these results indicate that rhythmic acoustic stimulation, by elevating spindle density, could reduce chronic pain symptoms.

Discussion

The appropriate assessment of pain, particularly chronic pain, is essential to understanding pain mechanisms and providing proper treatment. Current pain assessment in both humans and animal models relies on subjective verbal or behavioral reports. However, the development of objective neurophysiological measures can complement subjective behavioral measures to yield promising advances in the diagnosis and management of pain.

All sensory information received from the external environment, including nociception, passes through the thalamus before reaching the cortex. The thalamus, through its interaction with the cortex, has a long established role in attention and sensory gating mechanisms during sleep. Sleep spindle waves occur during NREM sleep, and they have been shown to play a role in learning, memory consolidation and sensory processing. Meanwhile, deficits in spindle activity during sleep have also been linked to numerous pathologies including epilepsy, altered mentation, poor memory retention, and other neuropsychiatric illness. Interestingly, recent studies have also demonstrated the role for sleep spindles may be in the attenuation of signals from the external environment, as a form of sensory gating. This role in sensory gating suggests the involvement for spindle waves in processing nociceptive inputs as well.

A number of studies have demonstrated a relationship between spindle density and sleep stability, with the underlying mechanisms being perturbations in thalamocortical oscillation. At the same time, an increasing number of studies have also shown that chronic pain is associated with poor sleep quality, especially interruptions in slow wave, NREM sleep. Since sleep spindle density has been implied in many functional roles in memory consolidation and sensory gating, it is important to accurately identify and characterize sleep spindles. Our SpindleNet can serve as an excellent spindle detector due to its robust performance. Our study makes the link between these two lines of inquiries. We found that depressed spindle waves are associated with chronic pain. Due to the role of spindles in sensory gating, cognition, and affect, through modulations of thalamocortical oscillation, it is quite plausible that deficits in spindle waves would contribute to the pathology or pathogenesis of chronic pain. Our finding that acoustic stimulation exposure can enhance spindle waves and over time decrease allodynia in rats with chronic pain provides further support for this hypothesis.

The use of EEG findings as a biomarker for neuropsychiatric diseases has gained considerable interest over the last decade. Compared with other neuroimaging modalities such as the MRI, EEG is cheaper, more portable and easier to use. Modern source localization has further improved the spatial resolution for high-density EEG studies, advancing the specificity and sensitivity of EEG biomarkers. Acute pain triggers characteristic evoked potentials (or event related potentials, ERPs) on the EEG, as well as elevated theta and gamma powers. More importantly, the power of theta and gamma oscillations are altered in chronic pain state, and changes in these EEG nociceptive response have been shown to predict the presence of pain and analgesic effects. Further, recent machine learning-driven feature extractions of EEG signals have been shown to distinguish pain patients and healthy controls. These studies support the use of EEG as a potential tool to derive biomarkers or biosignatures for pain. In this study we have demonstrated an unique use of spindle activity during sleep as an EEG finding for pain states. Sleep spindles can be measured easily at home or in the hospital, and can be used to track the presence and progression of pain symptoms. Future work in humans can validate the use of spindle density changes as a biomarker for chronic pain.

Our results also have therapeutic implications, as our strategy to enhance spindles is associated with decreased allodynia. Acoustic stimulation is non-invasive, and much research has been conducted in the use of acoustic stimuli to manipulate spindles, with multiple studies showing measurable behavioral impacts on memory and cognition in human subjects. However, protocols for spindle manipulation vary, with some groups utilizing bursts of white or pink noise as in this study, and others even implementing closed-loop electrical or acoustic stimulation in real-time. It is contemplated that the acoustic stimulation may be administered as a closed-loop acoustic stimulation, or may be random acoustic stimulation.

In summary, we have applied a deep neural network approach to automate the analysis of sleep spindles in rodents. Our study indicates that spindle density is decreased in the chronic pain state. Acoustic stimulation, meanwhile, can enhance spindles and relieve chronic pain symptoms. Therefore, our study suggests the potential for sleep spindles to function as targets for pain diagnosis and for therapeutic neuromodulation.

Materials and Methods
Rats

Experiments were conducted on male Sprague-Dawley rats obtained from Taconic Farms, Albany, N.Y. All procedures in this study were approved by the New York University School of Medicine (NYU SoM) Institutional Animal Care and Use Committee (IACUC) as consistent with the National Institute of Health (NIH) Guide for the Care and Use of Laboratory Animals to ensure minimal animal use and discomfort. Animals were given on average 14 days to acclimate to the facility prior to experimentation.

EEG Surgery

Rats were put under anesthesia (isoflurane, 1.5-2%) and placed in a stereotactic frame before undergoing implantation. A midline incision of 4 cm was made and several small screw-based electrodes were anchored on superficial holes drilled on the skull pertaining to PFC (Bregma +3.5 mm, midline) and bilateral hind-limb S1 (Bregma −2 mm, 2 mm lateral) regions. Screws were soldered to female Mill-Max connectors, and ground and reference screws were anchored above the cerebellum. Dental cement was used to secure equipment with bone screws. Rats were allowed to recover for at least 1 week after surgery.

Sleep Measurements

Sleep studies were performed over 4-5 hours in a quiet, isolated room in ambient temperature during the typical day cycle. The timing of recording was consistent throughout the course of study. Each rat was acclimated to sleep testing conditions in their home cage. Intan RHD2000 boards were connected to the rat at the start of the experiment and two video cameras recorded the rat for the duration of the experiment. Each rat received one week of acclimation, two days of baseline recordings, and experimental conditions were split between control and pain models. The pain model used was Complete Freund's Adjuvant (CFA). After baseline recordings, rats received CFA injection in the hind paw, and their sleep was measured 1, 3, and 7 days after injection.

Analysis

After isolating sleep using manual labeling of video, EEG time series acquired at 1 kHz were bandpass filtered and downsampled to 200 Hz then fed into a deep neural network (SpindleNet) to automatically detect spindle episodes. Spindle density was calculated as a measure of the number of spindles detected per minute of sleep recorded and normalized by average baseline recording data to calculate relative spindle density over time and compare across rats.

Allodynia Testing

Mechanical allodynia testing was performed using the Dixon up-down method with von-Frey filaments. Rats were placed on a mesh table, allowed to acclimate, and the hind limb paw was stimulated with filaments of logarithmically increasing stiffness. Withdrawal thresholds were recorded and 50% mechanical nociceptive threshold was computed, as described previously.

Pink Noise Stimulation

The stimuli were bursts of pink 1/f noise of 50 ms duration, with a 5-ms rising and falling time, respectively. Pink instead of white noise was used because it sounds softer and is therefore more comfortable to hear. Pink noise stimulation was performed using a computer speaker at fixed volume located near the rat in the controlled sleep environment. The noise file was generated by Audacity's built-in pink noise generator. Stimulation frequency was normalized from a gaussian distribution to a mean of 10 seconds between noises with a standard deviation of 3.33 seconds. Noise experiments were conducted at the end of a regular sleep recording session.

Spared Nerve Injury

Rats underwent a spared nerve injury (SNI) procedure, as described previously.[40,41] During the procedure, rats were anesthetized (isoflurane 2%). An inferomedial incision was made from the left knee to expose the sciatic nerve bundle. The branches of the sciatic nerve were identified, and the tibial and peroneal nerves were severed and tied off, sparing the sural nerve. Rats were allowed to recover for at least 1 week after surgery.

Sleep Staging

Video and accelerometer measurements of the rat's movement were used to classify sleep vs wake states. Among sleep periods, non-rapid eye movement (NREM) sleep was primarily determined by the high delta/theta EEG power ratio and the presence of slow waves and sleep spindles.

Automatic Spindle Detection

We used the method previously described in Example I, known as SpindleNet, to detect sleep spindles from a single-channel EEG. SpindleNet is a deep learning-based method for online detection of sleep spindles. SpindleNet consists of a convolution neural network (CNN) and recurrent neural network (RNN). It was operated and run on single-channel downsampled (200 Hz) sleep EEG signals. Compared to other state-of-the-art detection methods, SpindleNet can achieve low detection latency and high detection accuracy and specificity. In addition, SpindleNet can produce robust performance with various EEG sampling frequencies and signal-to-noise ratio (SNR). SpindleNet was run on a Linux computer with an embedded Nvidia GPU card.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method, performed by a processing arrangement, for administering stimulations to a sleeping subject, comprising the steps of:
    (i) obtaining brain wave data generated based on brain wave activity of the subject over a predetermined time frame ($T_w$), wherein the brain wave data is received from a brain wave sensor;
    (ii) determining a spectral power ratio of a spindle band to delta and theta bands of the brain wave data at a time within the predetermined time frame $T_W$, wherein the spectral power ratio is determined by at least one computer processor core;
    (iii) inputting the spectral power ratio and the brain wave data into a pretrained deep neural network, wherein the pretrained deep neural network is trained based on at least one set of input data and corresponding output data, the input data comprising reference brain wave data and the output data corresponding to a determination of presence or absence of sleep spindles based on the input data;
    (iv) generating a probability score that sleep spindles are being detected in the brain wave activity by comparing features extracted from the brain wave data of the subject to learned spectrotemporal features of the pretrained deep neural network, wherein the probability score is generated by the at least one computer processor core;
    (v) continuously repeating steps (i) to (iv) and determining a presence of sleep spindles is detected when the probability score is above a predetermined threshold score over a predetermined threshold period of time; and
    (vi) administering a brain stimulation to the subject when the presence of sleep spindles is detected.

2. The method of claim 1, wherein the brain wave data is EEG data.

3. The method of claim 2, wherein the brain wave data is generated from a single channel EEG.

4. The method of claim 1, wherein the deep neural network comprises a convolutional neural network followed sequentially by a recurrent neural network.

5. The method of claim 1, wherein the spectral power ratio is determined at a time $T_W/2$.

6. The method of claim 1, wherein the brain stimulation comprises at least one of acoustic stimulation and non-invasive transcranial brain stimulation.

7. The method of claim 6, wherein the brain stimulation is an acoustic stimulation configured to enhance sleep spindles or boost memory consolidation, without waking the subject.

8. The method of claim 6, wherein the brain stimulation is an acoustic stimulation configured to reduce chronic pain by stimulating elevation of spindle density.

9. The method of claim 8, wherein the brain stimulation is a rhythmic acoustic stimulation.

10. The method of claim 6, wherein the brain stimulation is a low frequency acoustic stimulation.

11. The method of claim 10, wherein the acoustic stimulation is pink noise.

12. The method of claim 11, wherein the acoustic stimulation is random pink noise based on a Gaussian random distribution.

13. A device for detection of sleep spindles in a subject, comprising:
    a sensor configured to generate brain wave data corresponding to brain wave activity of the subject; and
    a processor operably connected to the sensor and configured to (i) obtain the brain wave data from the sensor over a predetermined time frame, (ii) determine a spectral power ratio of a spindle band to delta and theta bands of the brain wave data at a time within the predetermined time frame, (iii) input the spectral power ratio and the brain wave data into a pretrained deep neural network to generate a probability score that sleep spindles are being detected in the brain wave activity, and (iv) generate the probability score that sleep spindles are being detected in the brain wave activity by comparing features extracted from the brain wave data of the subject to learned spectrotemporal features of the pretrained deep neural network; (v) continuously repeating (i) to (iv) and determining a presence of sleep spindles is detected when the probability score is above a predetermined threshold score over a predetermined threshold period of time, wherein the pretrained deep neural network is trained based on at least one set of input data and corresponding output data, the input data comprising reference brain wave data and the output data corresponding to a determination of presence or absence of sleep spindles based on the input data; and (vi) administering a brain stimulation to the subject when the presence of sleep spindles is detected.

14. A method, performed by a processing arrangement, for detecting chronic pain in a subject, comprising the steps of:
    (i) obtaining brain wave data generated based on brain wave activity of the subject over a predetermined time frame ($T_W$) during sleep, wherein the brain wave data is received from a brain wave sensor;
    (ii) determining a spectral power ratio of a spindle band to delta and theta bands of the brain wave data at a time within the predetermined time frame $T_W$, wherein the spectral power ratio is determined by at least one computer processor core;
    (iii) inputting the spectral power ratio and the brain wave data into a pretrained deep neural network to generate a probability score that sleep spindles are being detected in the brain wave activity, wherein the pretrained deep neural network is trained based on at least one set of input data and corresponding output data, the input data comprising reference brain wave data and the output data corresponding to a determination of presence or absence of sleep spindles based on the input data;

(iv) generating the probability score that sleep spindles are being detected in the brain wave activity by comparing features extracted from the brain wave data of the subject to learned spectrotemporal features of the pretrained deep neural network, wherein the probability score is generated by the at least one computer processor core;

(v) continuously repeating steps (i) to (iv) and determining a presence of sleep spindles is detected when the probability score is above a predetermined threshold score over a predetermined threshold period of time;

(vi) quantifying a severity of pain based on density of the sleep spindles detected in steps (i) to (v); and (vi) administering a brain stimulation to the subject based on the severity of pain.

15. The method of claim 14, wherein the brain stimulation is a low frequency acoustic stimulation.

16. The method of claim 15, wherein the acoustic stimulation is pink noise.

17. The method of claim 16, wherein the acoustic stimulation is random pink noise based on a Gaussian random distribution.

18. The method of claim 14, wherein the deep neural network comprises a convolutional neural network followed sequentially by a recurrent neural network.

19. The method of claim 14, wherein the spectral power ratio is determined at a time $T_W/2$.

* * * * *